United States Patent
Liu

(10) Patent No.: US 12,251,234 B2
(45) Date of Patent: Mar. 18, 2025

(54) SYSTEMS AND METHODS FOR TRANSDERMALLY DETECTING TISSUE ISCHEMIA AND EVALUATING ORGAN FUNCTION USING SERUM LUMINESCENCE

(71) Applicants: University of Macau, Taipa (CN); CATYDID Technology Ltd., Taipa (CN)

(72) Inventor: Tzu-Ming Liu, Taipa (CN)

(73) Assignees: University of Macau, Taipa (CN); CATYDID Technology Ltd., Taipa (CN)

( * ) Notice: Subject to any disclaimer, the term of this patent is extended or adjusted under 35 U.S.C. 154(b) by 1118 days.

(21) Appl. No.: 16/577,996

(22) Filed: Sep. 20, 2019

(65) Prior Publication Data
US 2020/0093415 A1 Mar. 26, 2020

Related U.S. Application Data

(60) Provisional application No. 62/734,961, filed on Sep. 21, 2018.

(51) Int. Cl.
*A61B 5/00* (2006.01)
*G01N 21/64* (2006.01)

(52) U.S. Cl.
CPC .......... *A61B 5/4244* (2013.01); *A61B 5/0071* (2013.01); *A61B 5/489* (2013.01); *A61B 5/7203* (2013.01); *G01N 21/6428* (2013.01); *G01N 2021/6417* (2013.01)

(58) Field of Classification Search
CPC ............. A61B 5/0071; G01N 21/6428; G01N 21/6486
See application file for complete search history.

(56) References Cited

U.S. PATENT DOCUMENTS

| 2009/0093807 A1* | 4/2009 | Hyde | A61B 5/0084 |
| | | | 606/34 |
| 2012/0209090 A1* | 8/2012 | Goodall | A61B 5/14503 |
| | | | 604/523 |

OTHER PUBLICATIONS

Nitta et al Intelligent Image-Activated Cell Sorting, 2018, Cell 175, 266-276 Sep. 20, 2018 ª 2018 Elsevier Inc.*

* cited by examiner

Primary Examiner — Serkan Akar
(74) Attorney, Agent, or Firm — Getech Law LLC; Jun Ye

(57) ABSTRACT

Methods for the early sensing of tissue ischemia and/or infarctions within organs using the spectroscopic features of serum luminescence include (i) isolating serum from a blood sample, (ii) directing an excitation light at the serum, (iii) receiving an endogenous serum chromophore emission light from the excited serum, and (iv) determining a presence of an ischemic condition based on the intensity of the endogenous serum chromophore emission light. Methods of detecting organ dysfunction can include transmitting excitation light to luminal contents of a mammalian blood vessel comprising trace amounts of exogenous chromophores administered to the subject mammal via the circulatory system. Transdermal luminescence measurements from the trace amounts of exogenous chromophores can then be used to determine organ dysfunction. Such methods enable routine monitoring of blood luminescence to bridge the diagnosis gap between sensitive symptom diagnosis and specific marker diagnosis, resulting in an effective early screening modality.

4 Claims, 18 Drawing Sheets
(17 of 18 Drawing Sheet(s) Filed in Color)

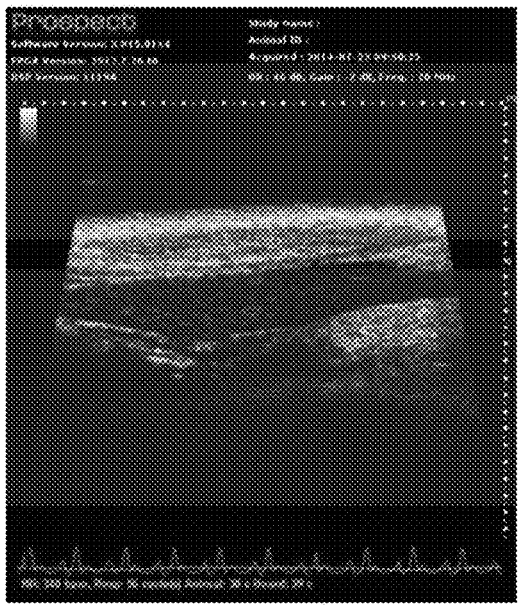
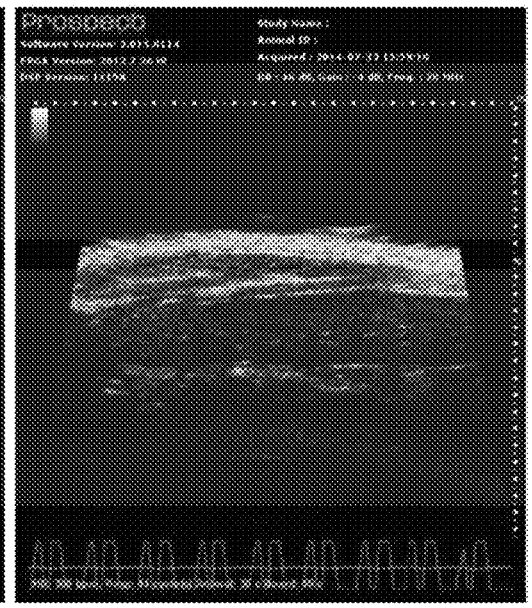
FIG. 17A                    FIG. 17B
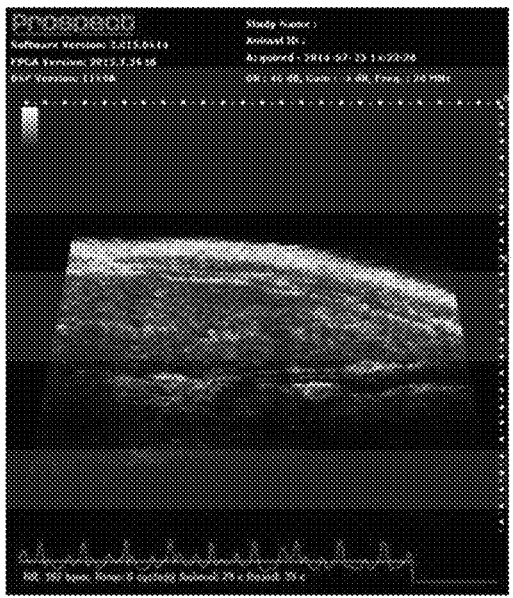
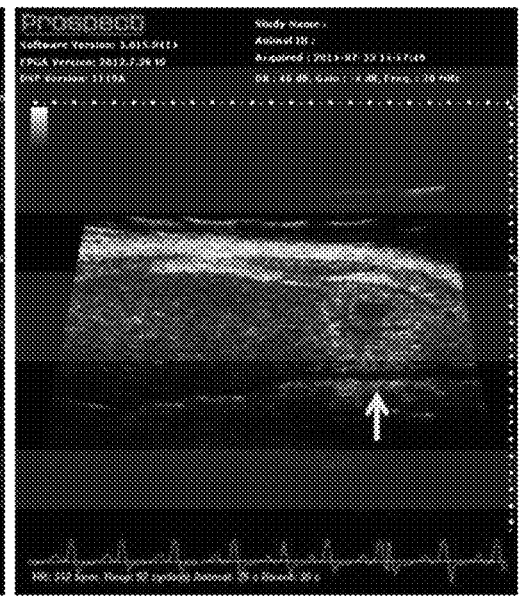
FIG. 17C                    FIG. 17D

[PRIOR ART]

SYSTEMS AND METHODS FOR TRANSDERMALLY DETECTING TISSUE ISCHEMIA AND EVALUATING ORGAN FUNCTION USING SERUM LUMINESCENCE

CROSS-REFERENCE TO RELATED APPLICATIONS

This application claims priority to and the benefit of U.S. Provisional Patent Application Ser. No. 62/734,961, filed Sep. 21, 2018 and titled "A SERUM LUMINESCENCE APPROACH TO DETECT THE TISSUE ISCHEMIA AND EVALUATE THE ORGAN FUNCTION," which is incorporated herein by this reference in its entirety.

BACKGROUND

Technical Field

This disclosure generally relates to the non-invasive detection and/or evaluation of organ function. More specifically, this disclosure relates to the non-invasive detection of tissue ischemia from serum luminescence to detect and/or evaluate organ dysfunction.

Related Technology

The rate of organ failure after liver transplantation has historically been around 32%. Patients who experience organ failure following liver transplantation have an average mortality rate of about 42% compared to the 2% mortality rate of patients without organ failure. Among the organs that fail following liver transplantation, kidneys appear relatively sensitive with roughly 30-50% of acute renal failure occur after liver transplantation. The foregoing illustrates that ischemia-reperfusion damage induced organ failures are major risks associated with organ transplantation.

Thrombosis or embolism caused by obstruction of blood flow from plaques, blood clots, fat emboli, foreign objects, or other bodily substance within the circulation system may also induce organ failure. Strokes and myocardial infarction are two major types of internal ischemia and are relatively easy to diagnose from physiological symptoms. Other ischemia, such as bowel ischemia or acute mesenteric ischemia, are more difficult to diagnose due to non-specific symptoms like abdominal pain. This can be problematic as late diagnosis is associated with a 60-80% mortality rate. Similarly, deep vein thrombosis can lead to a lethal pulmonary embolism, but there is a lack of distinctive physiological symptoms to enable rapid and accurate diagnoses of deep vein thrombosis. Early diagnosis can help physicians to prescribe or administer anticoagulant therapy and save patients' lives.

Typically, intensive care physicians rely on a physiological monitor to screen for these kinds of critical conditions. However, such screening requires constant monitoring and the interpretation of multiple systems, such as blood pressure, electrocardiography (ECG), and blood oxygen saturation. None of these systems in isolation can specifically provide the diagnostic information needed to accurately and consistently identify the development or presence of ischemia, particularly at an early stage where intervention has a higher likelihood of success. Instead, by the time such disordered physiology can be determined using traditional multi-system physiological monitoring systems, the mortality rate is high. Accumulation of free radicals within the circulation system and systemically activated neutrophils may lead to irreversible shocks. In vitro assaying of serum marker proteins may help with an earlier differential diagnosis, but the traditional in vitro assays are usually time-consuming and expensive. It is cost prohibitive and inefficient to routinely perform in vitro diagnosis in critical care.

Accordingly, there is an urgent need to develop a sensitive assay to screen for ischemia and/or infarctions within organs, particularly at an early stage.

BRIEF SUMMARY

Embodiments of the present disclosure solve one or more of the foregoing or other problems in the art with detecting tissue ischemia and/or evaluating organ dysfunction. In particular, one or more embodiments can include methods for detecting tissue ischemia within a mammal by at least (i) isolating serum from a blood sample, (ii) directing an excitation light at the serum, (iii) receiving an endogenous serum chromophore emission light from the excited serum, and (iv) determining a presence of an ischemic condition based on an intensity of the endogenous serum chromophore emission light.

In one aspect, determining the presence of the ischemic condition includes calculating an optical index, which is an arithmetic calculation of spectral intensities at a plurality of wavelengths that are each associated with a principle chromophore component determined from an excitation wavelength swept fluorescence spectra of the blood sample.

Additionally, or alternatively, determining the presence of the ischemic condition can include determining that the intensity of the endogenous serum chromophore has exceeded a threshold intensity level, comparing the intensity of the endogenous serum chromophore emission light to a baseline emission intensity and determining the value of the baseline emission intensity to be lower than the intensity of the endogenous serum chromophore emission light, and/or comparing a real-time measurement of the intensity of the endogenous serum chromophore emission light to a first timepoint or a predetermined value associated with a non-ischemic condition.

In one aspect, isolating serum includes isolating serum at a catheter to repeatedly or constantly measure the intensity of the endogenous serum chromophore such that the presence of an ischemic condition is determined contemporaneously with the real time detection that the intensity of the endogenous serum chromophore has exceeded a threshold intensity level. In some instances, if the ischemic condition determined to be present, the disclosed methods can additionally include conducting an in vitro assay of serum marker proteins to confirm a type and/or anatomical location of the tissue ischemia. Alternatively, if the ischemic condition is determined not to be present (or has yet to be determined as present), the methods of the present disclosure can include continuing to monitor the endogenous serum chromophore emission light of serum isolated at later timepoints.

In one aspect, isolating serum includes routing blood from a central venous/artery catheter to a microfluidic chip configured to separate the serum from the routed blood.

In one aspect, the methods additionally include implementing appropriate treatment or medical intervention based on the determination of ischemia and/or organ dysfunction.

Methods for detecting an infarction or organ dysfunction can include (i) administering to a mammal of a trace amount of an exogenous chromophore, (ii) identifying a blood vessel within the mammal, (iii) transmitting excitation light to the luminal contents of the blood vessel comprising the exogenous chromophore, (iv) obtaining a transdermal measurement of the exogenous chromophore, and (v) based on the transdermal luminescence measurement, determining organ dysfunction.

In one aspect, the trace amount of the exogenous chromophore is administered intravenously and can be indocyanine green (ICG), fluorescein, and/or methylene blue. For example, the exogenous chromophore can be ICG administered intravenously to an in vivo concentration at or below about $10^{-3}$ mg/mL.

In one aspect, the transdermal luminescence measurement of the chromophore is received through a lip, nail fold, ear lobe, or other dermal location of the mammal having a rich network of blood vessels and fewer pigments.

In one aspect, determining organ dysfunction based on the transdermal luminescence measurement includes the step of comparing the transdermal luminescence measurement to a healthy, expected luminescence measurement calculated from a known chromophore decay constant and based on an amount of time following administration of the solution.

Embodiments of the present disclosure additionally include systems for performing non-invasive detection of liver dysfunction. An exemplary system includes (i) an excitation light configured to excite an exogenous chromophore within one or more blood vessels located at a target area of a mammal, (ii) an objective lens configured to receive luminescence signals from an excited exogenous chromophore within the one or more blood vessels, (iii) a tissue mount associated with the objective lens that includes an air suction channel configured to pull a negative pressure for attaching the tissue mount to the target area and fixing an axial distance between the one or more blood vessels and the objective lens, and (iv) a computer system with at least one or more processors and one or more hardware storage devices having stored thereon computer-executable instructions that, when executed by at least one of the one or more processors, configure the computer system to at least (a) direct the excitation light to excite the exogenous chromophore, (b) automatically identify the one or more blood vessels within the target area using a line scanning or circular contour scanning module comprising scanning mirrors and lenses configured to steer the excitation light within the target area, (c) receive a plurality of luminescence signals at a photodetector electronically coupled to the computer system and positioned in an emission light path of the objective lens, (d) calculate a dosimetry curve based on the plurality of luminescence signals received at the photodetector, and (e) determine liver dysfunction based on the dosimetry curve as compared to a standard decay constant of the exogenous chromophore within a healthy mammal.

In one aspect, the exogenous chromophore is ICG and the system is configured to determine liver dysfunction based on an in vivo concentration of ICG between about $10^{-4}$ mg/mL to about $10^{-7}$ mg/mL.

In one aspect, the system additionally includes an adaptor configured in size and shape to couple to luminescence measurement apparatuses, which can include the excitation light, the objective lens, the tissue mount, and/or the photodetector, among other luminescence measurement apparatuses. The adaptor can associate with a transparent port or branch part of a central venous/artery catheter. Additionally, or alternatively, the system includes a microfluidic chip configured to separate the serum from blood routed through a transparent port or branch part of the central venous/artery catheter.

In one aspect, the system additionally includes one or more band pass filters, notch filters, or long pass filters for blocking residual excitation light.

Accordingly, systems and method for the detection (and treatment) of tissue ischemia and/or organ dysfunction are disclosed. This summary is provided to introduce a selection of concepts in a simplified form that are further described below in the detailed description. This summary is not intended to identify key features or essential features of the claimed subject matter, nor is it intended to be used as an indication of the scope of the claimed subject matter.

Additional features and advantages of the disclosure will be set forth in the description which follows, and in part will be obvious from the description, or may be learned by the practice of the disclosure. The features and advantages of the disclosure may be realized and obtained by means of the instruments and combinations particularly pointed out in the appended claims. These and other features of the present disclosure will become more fully apparent from the following description and appended claims or may be learned by the practice of the disclosure as set forth hereinafter.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

In order to describe the manner in which the above recited and other advantages and features of the disclosure can be obtained, a more particular description of the disclosure briefly described above will be rendered by reference to specific embodiments thereof, which are illustrated in the appended drawings. It is appreciated that these drawings depict only typical embodiments of the disclosure and are not therefore to be considered to be limiting of its scope.

Figure 1:
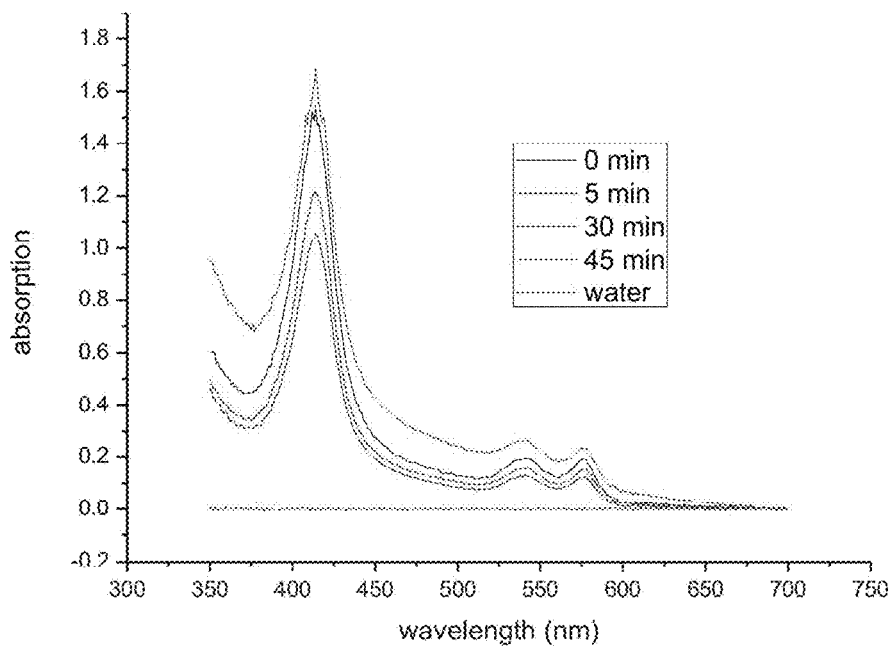

The disclosure will be described and explained with additional specificity and detail through the use of the accompanying drawings in which:

FIG. 1 illustrates the absorption spectrum of water and rat serum at 0-, 5-, 20-, and 45-minutes post mesenteric ischemia.

Figure 2:
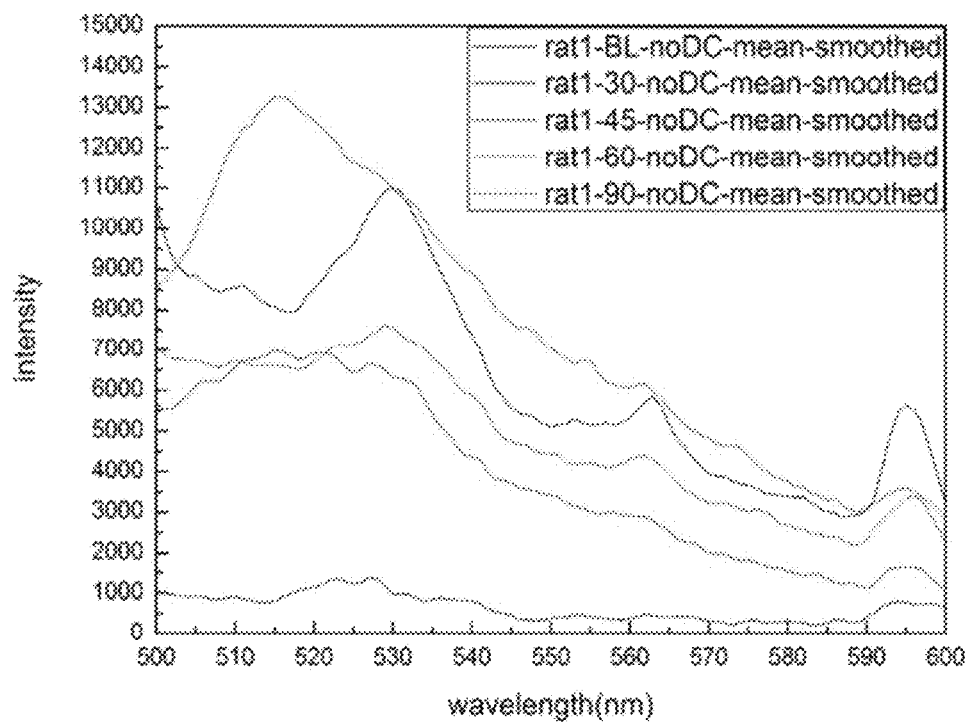

FIG. 2 illustrates the fluorescence excitation spectra of baseline rat serum (BL) and at 30-, 45-, 60-, and 90-minutes post ischemia.

Figure 3:
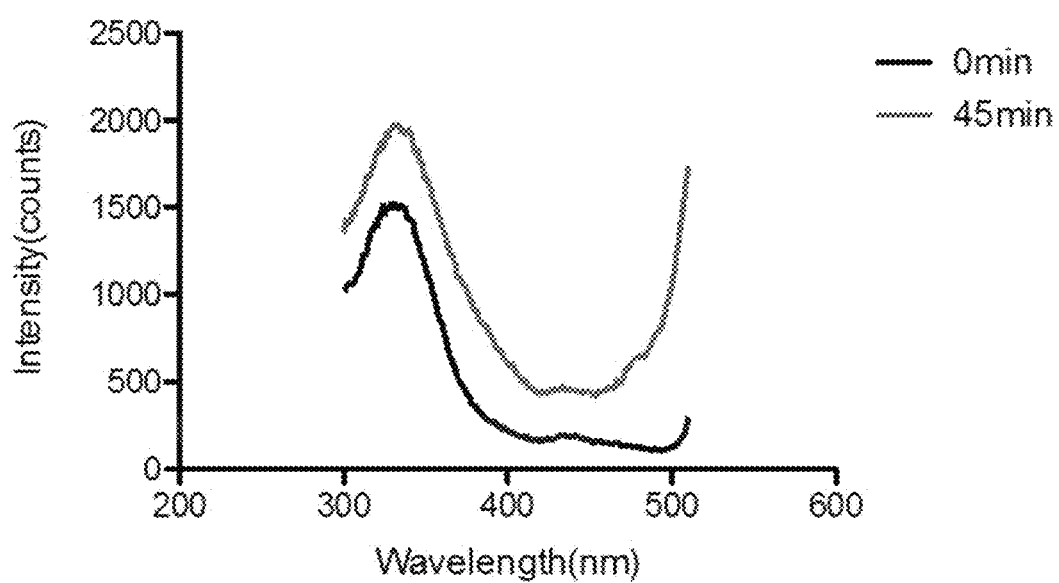

FIG. 3 illustrates the fluorescence excitation spectra of rat serum at 0- and 45-minutes post mesenteric ischemia.

Figure 4A:
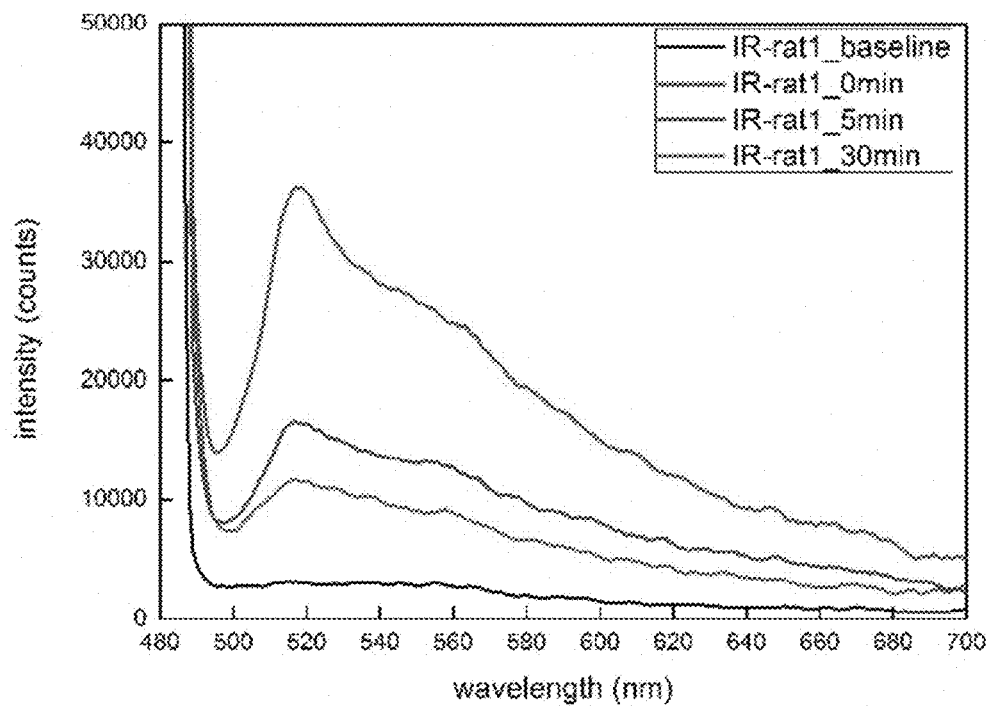
Figure 4B:
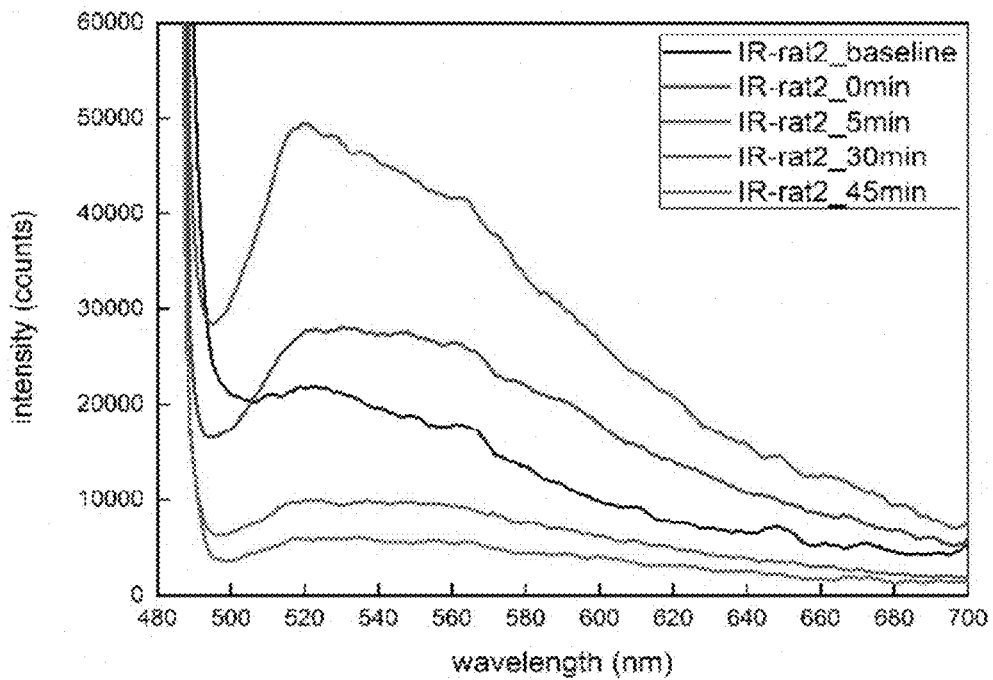

FIGS. 4A and 4B respectively illustrate the fluorescence spectra of baseline serum and of serum collected 0-, 5-, 30-, and 45-minutes post ischemia-reperfusion (IR) from two rats.

Figure 5A:
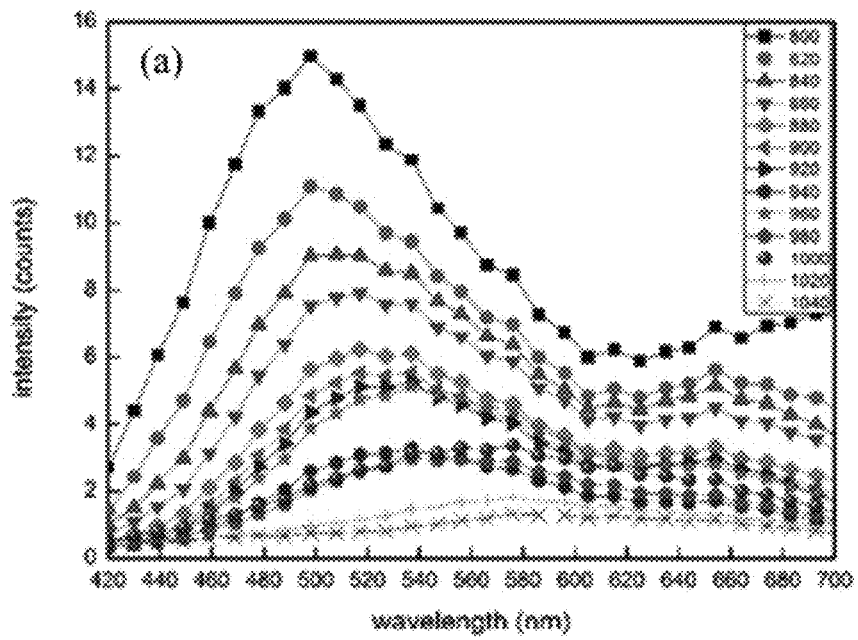
Figure 5B:
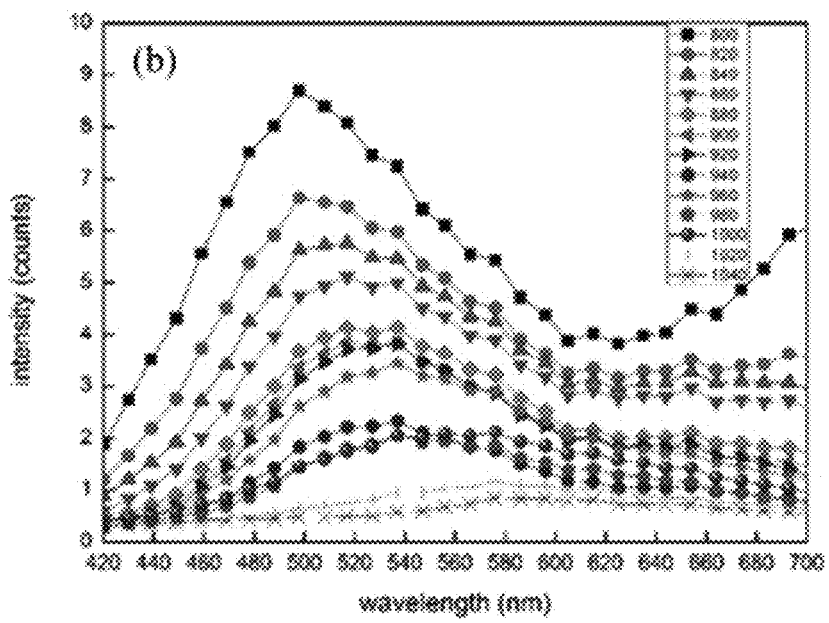

FIGS. 5A and 5B illustrate the two-photon fluorescence spectra of baseline serum sampled from two rats. The excitation wavelength was tuned from 800 nm to 1040 nm with equalized excitation intensity.

Figure 6A:
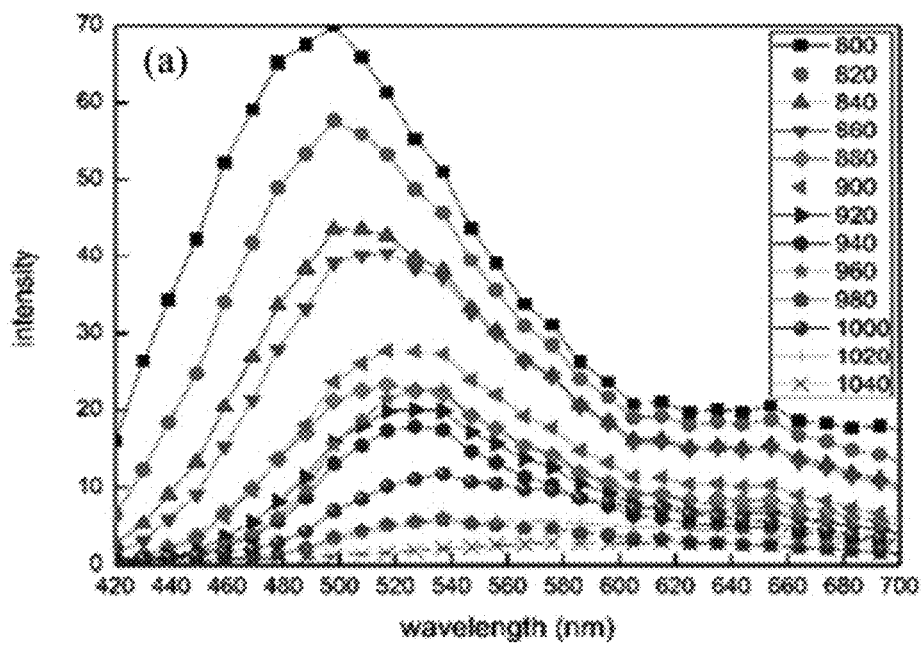
Figure 6B:
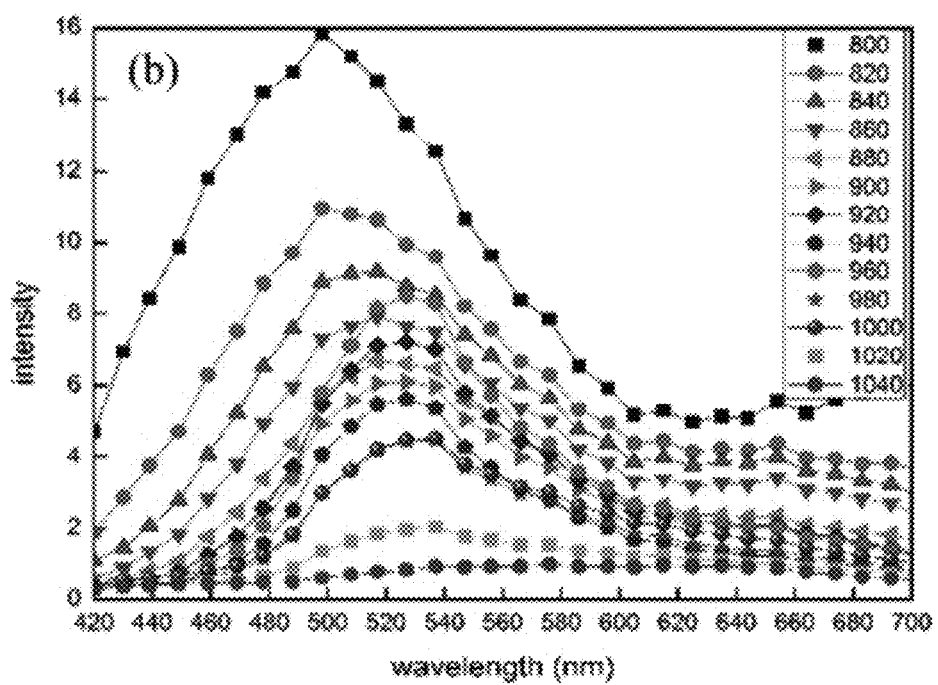

FIG. 6A illustrates the two-photon fluorescence spectra of rat serum 90-minutes post mesenteric ischemia. FIG. 6B illustrates the two-photon fluorescence spectra of rat serum 75-minutes post mesenteric ischemia. In each of FIGS. 6A and 6B, the excitation wavelength was tuned from 800 nm to 1040 nm with equalized excitation intensity.

Figure 7A:
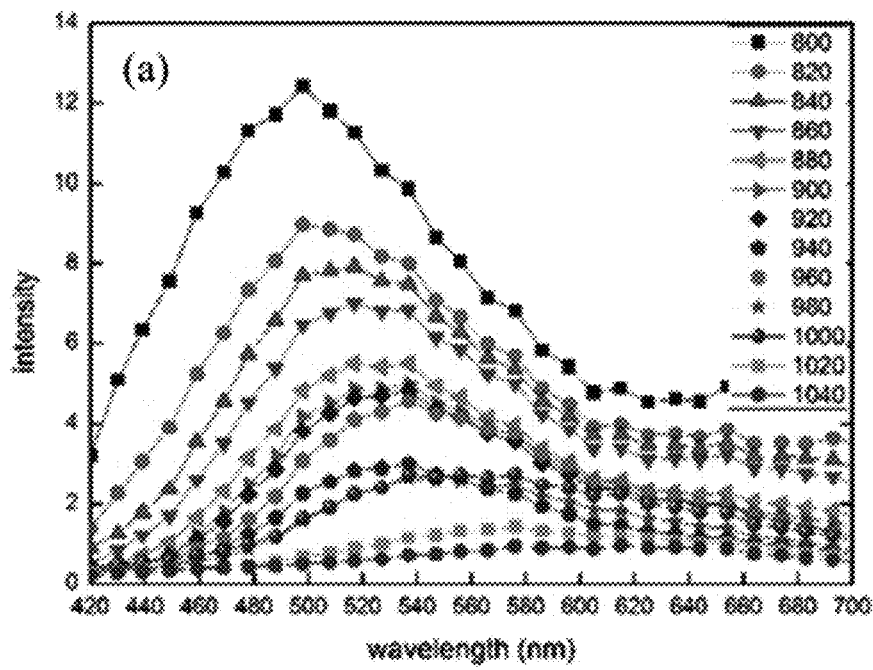
Figure 7B:
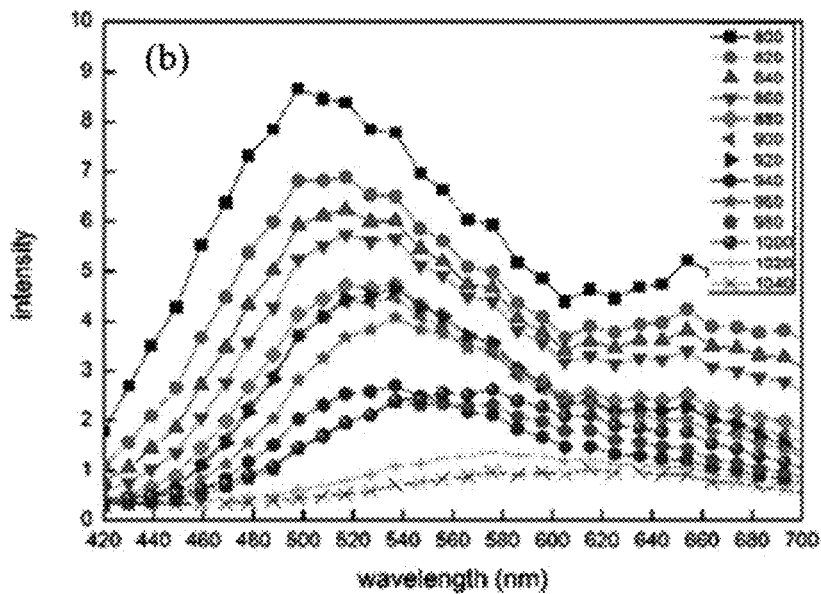

FIGS. 7A and 7B illustrate the two-photon fluorescence spectra of rat serum 45-minutes post ischemia-reperfusion sampled from two rats. The excitation wavelength was tuned from 800 nm to 1040 nm with equalized excitation intensity.

Figure 8A:
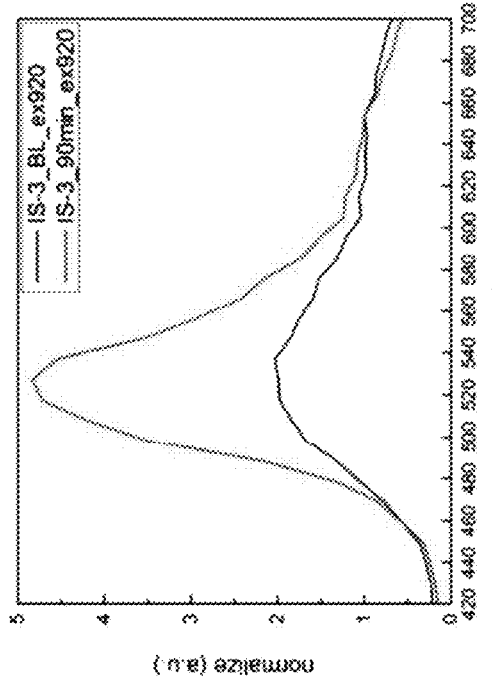
Figure 8B:
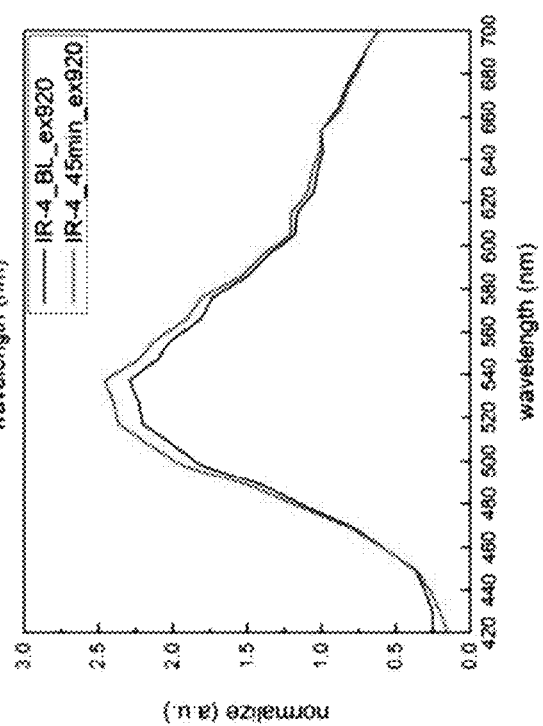

FIGS. 8A-8D illustrate two-photon fluorescence (ex@920 nm) spectra of rat serum normalized to the intensity at 654 nm. FIGS. 8A and 8B illustrate two-photon fluorescence spectra of serum isolated from two rats at baseline (BL, black curve) and at 90-minutes post ischemia (IS, red curve).

Figure 8C:
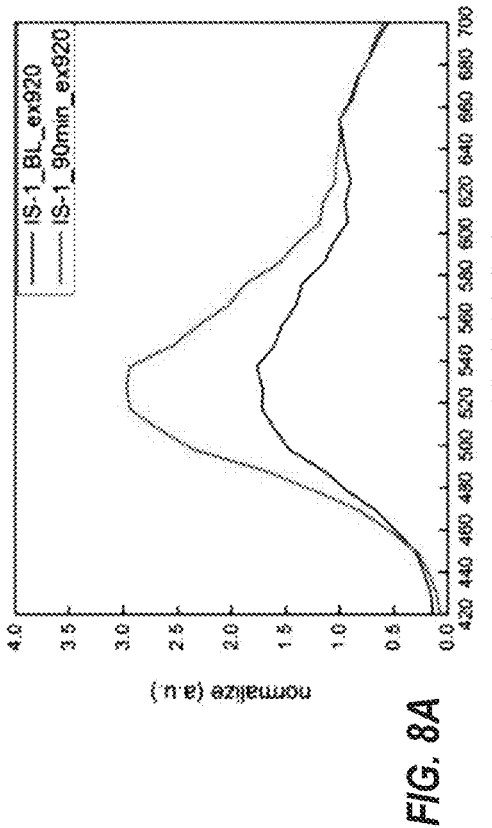
Figure 8D:
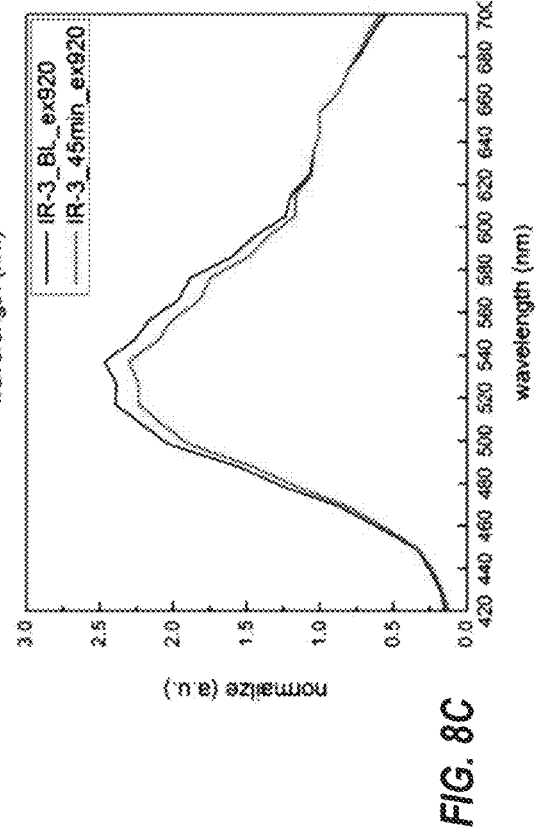

FIGS. 8C and 8D illustrate two-photon fluorescence spectra of serum isolated from two rats at baseline (BL, black curve) and at 45-minutes post ischemia reperfusion (IR, red curve).

Figure 9A:
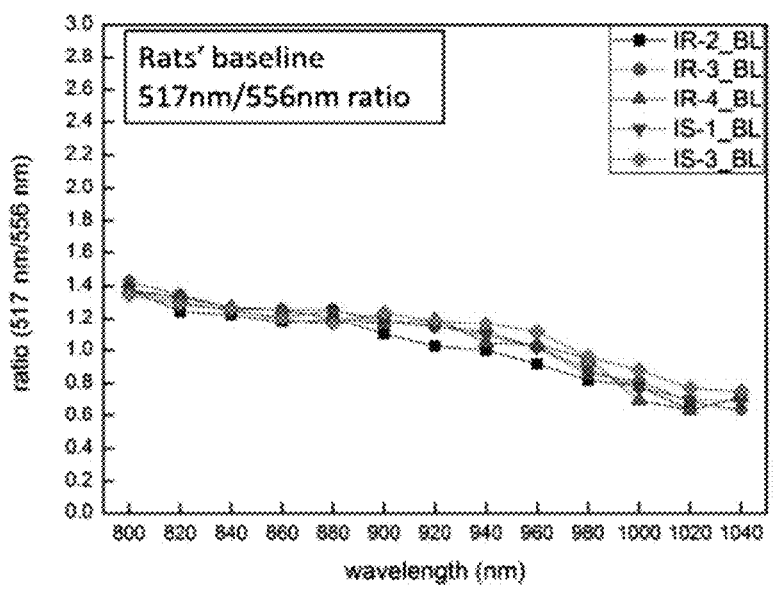
Figure 9B:
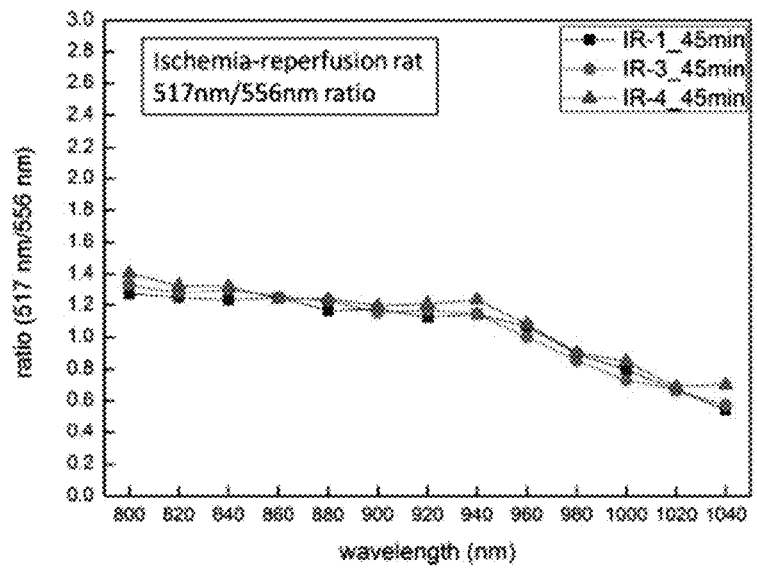
Figure 9C:
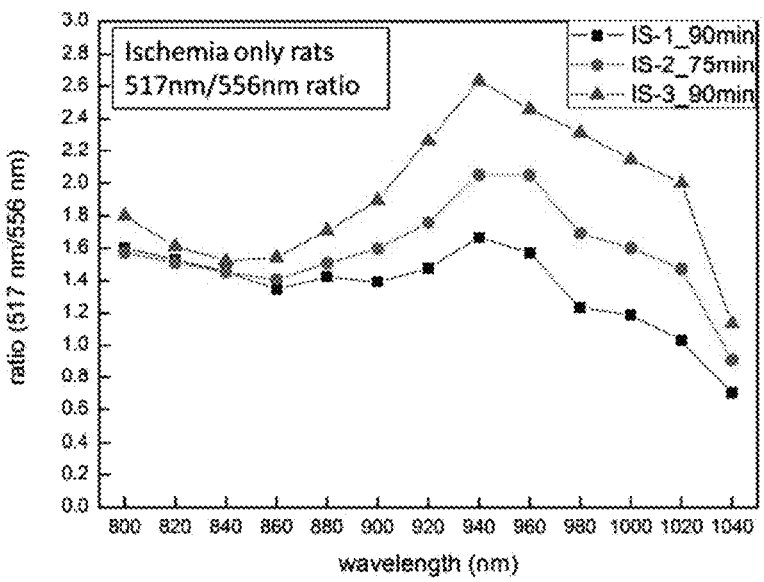

FIGS. 9A-9C illustrate the 517/556 nm ratio of two-photon fluorescence spectra at different excitation wavelengths. The two-photon fluorescence spectra were obtained from baseline rat serum prior to any reperfusion (FIG. 9A), from rat serum 45-minutes post ischemia-reperfusion (FIG. 9B), and from rat serum 75- or 90-minutes post ischemia (FIG. 9C).

Figure 10A:
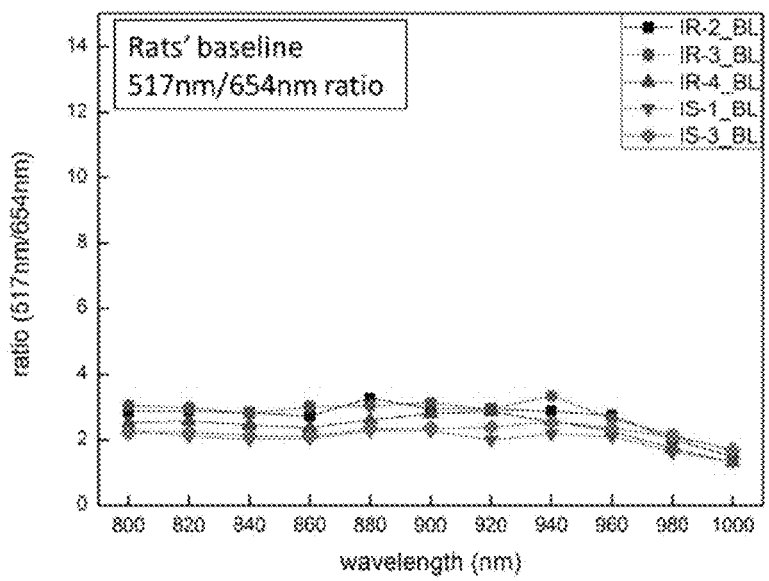
Figure 10B:
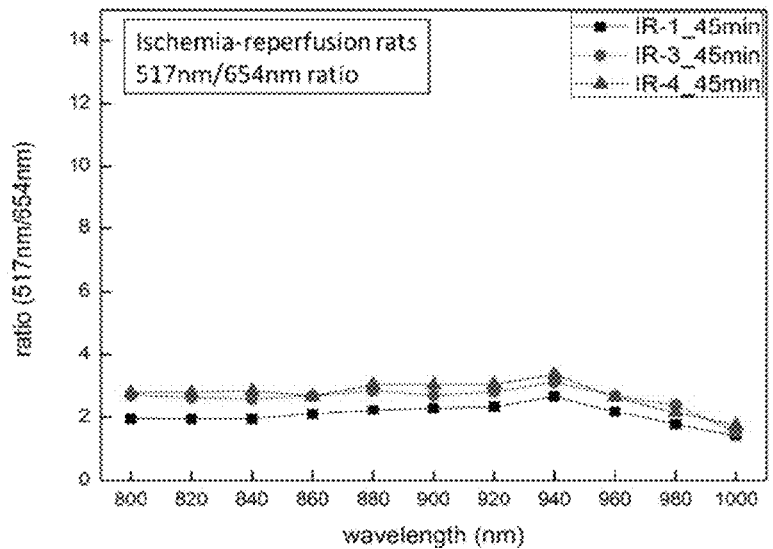
Figure 10C:
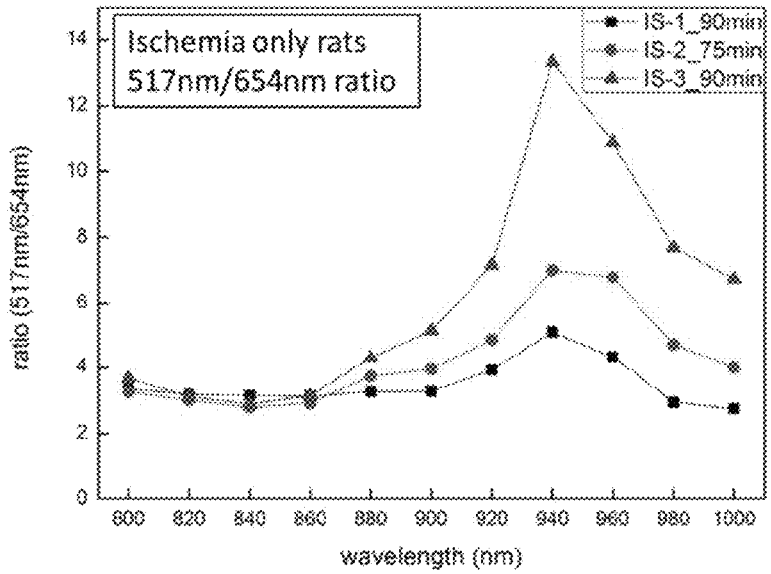

FIGS. 10A-10C illustrate the 517/654 nm ratio of the two-photon fluorescence spectra from FIGS. 9A-9C, respectively.

Figure 11:
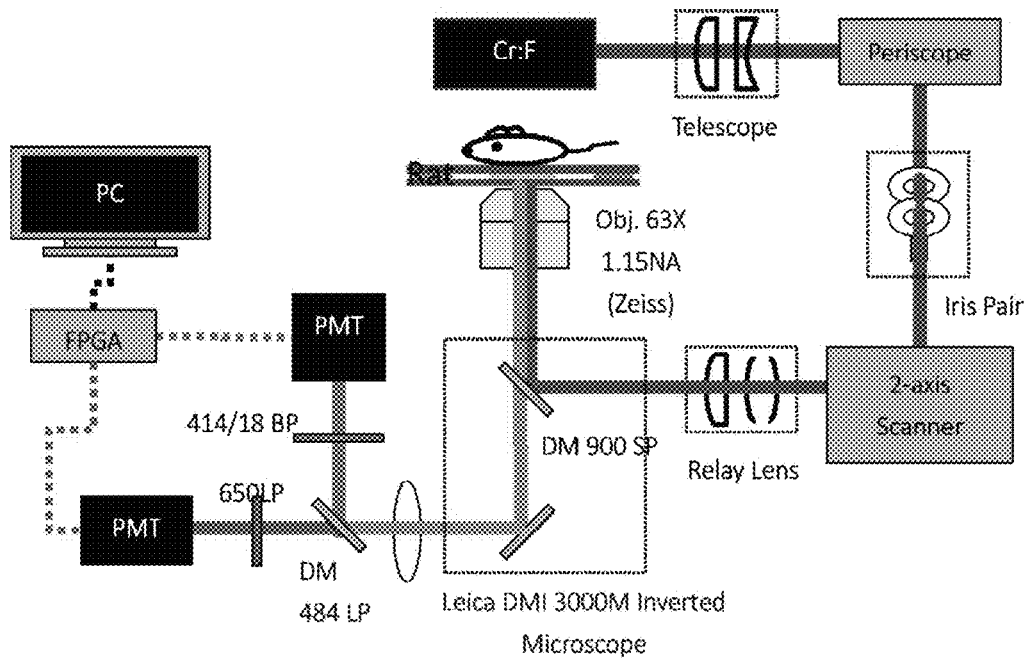

FIG. 11 is a diagram representing an exemplary multiphoton microscopy system for in vivo angiography with indocyanine green. As illustrated, DM: dichroic mirror; LP: long pass filter; BP: bandpass filter; PMT: photomultiplier tubes; and FPGA: field programmable gate array.

Figure 12:
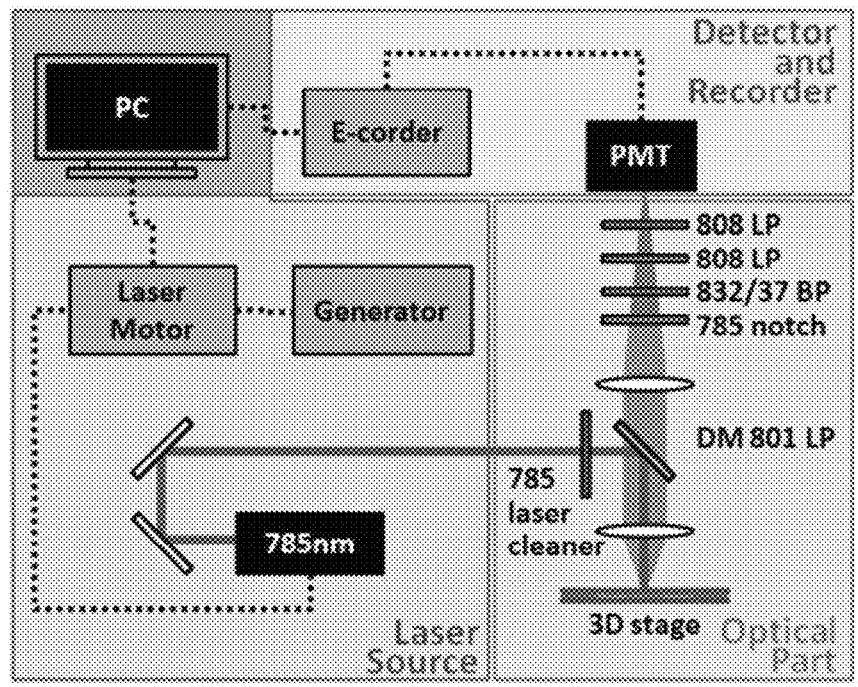

FIG. 12 is a diagram representing a point excitation measurement system. As illustrated, DM: dichroic mirror; LP: long pass filter; BP: bandpass filter; PMT: photomultiplier tube.

Figure 13:

FIG. 13 is a photograph illustrating an implementation of the point excitation measurement system of FIG. 12 where excitation of the luminal contents of a blood vessel located in a mouse ear was performed using a 785 nm continuous wave laser.

Figure 14:
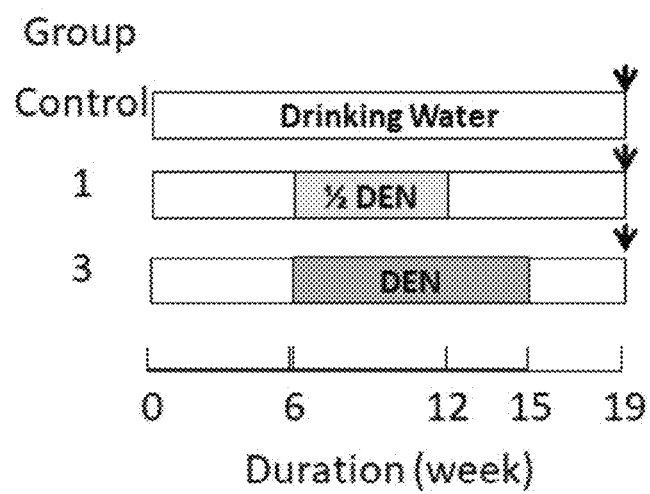

FIG. 14 is a schematic of an administration schedule for the disclosed hepatocellular carcinoma rat model. As illustrated, the arrow indicates the sacrificial timepoint and DEN: N-Nitrosodiethylamine, ½ DEN: half dosage of N-Nitrosodiethylamine.

Figures 15A, 15B, 15C:
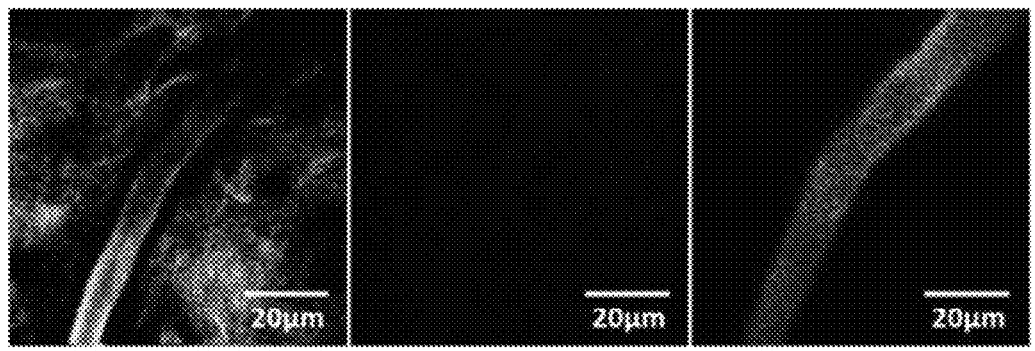

FIGS. 15A-C are micrographs of rat tissue. FIG. 15A is a micrograph obtained using third harmonic generation (THG) imaging to demonstrate the ability of THG to locate blood vessels from resident blood cell THG signaling. FIGS. 15B and 15C are two photon fluorescent (TPF) micrographs of the same viewing area shown in FIG. 15A before and after injection of ICG, respectively.

Figure 16:
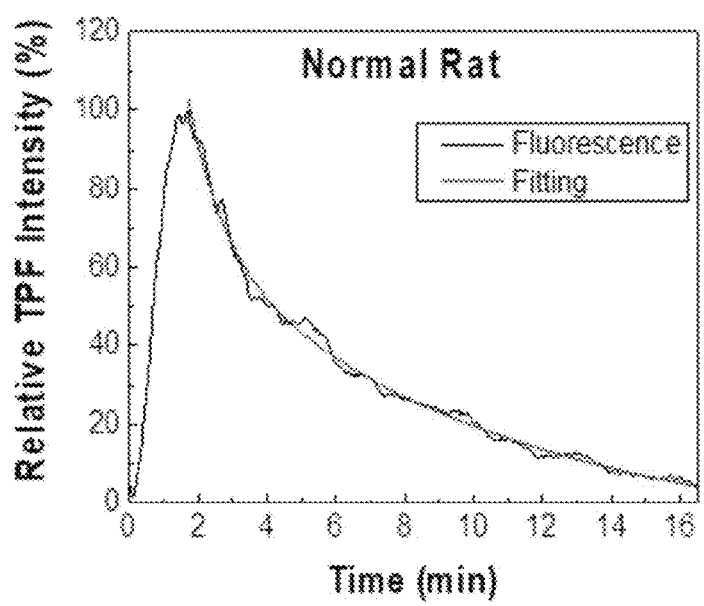

FIG. 16 is a ICG TPF dosimetry curve (black curve) fit with a single exponential decay function (red curve).

FIGS. 17A-17D are ultrasound images of rat livers taken from rats in the hepatocellular carcinoma rat model illustrated in FIG. 14. A healthy control rat liver is shown in FIG. 17A, a rat liver from Group 1 is shown in FIG. 17B, and rat livers from Group 3 are shown in FIGS. 17C and 17D with a visible nodule being indicated by the yellow arrow in FIG. 17D.

Figure 18:
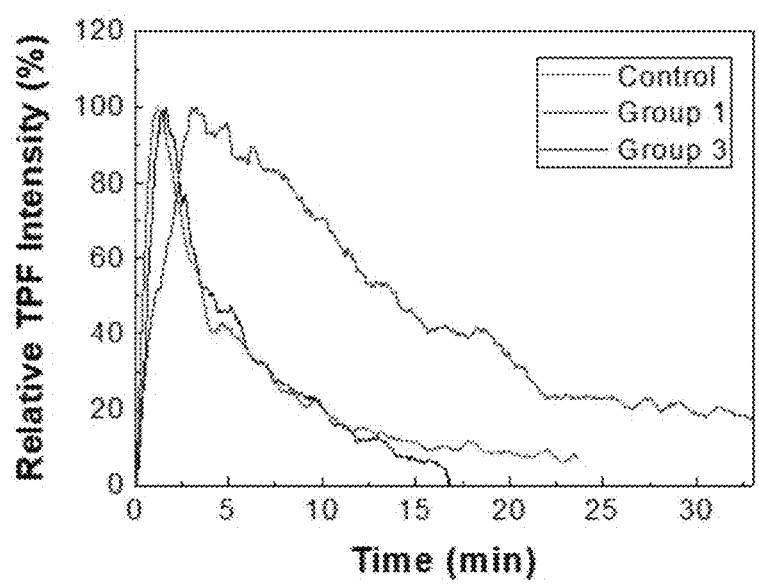

FIG. 18 is a fluorescence dosimetry curve of ICG retention for rats in the Control group (black curve), Group 1 (red curve), and Group 3 (blue curve).

Figure 19A:
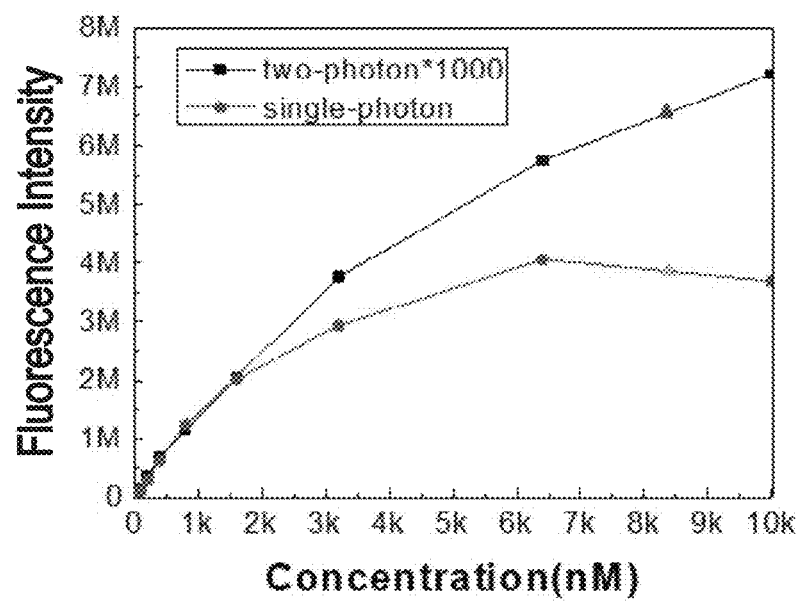
Figure 19B:
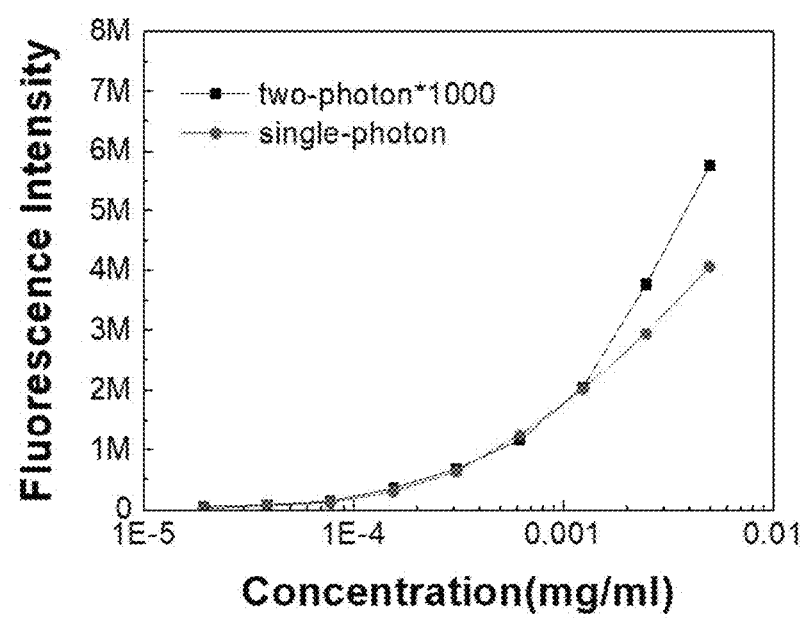
Figure 20A:
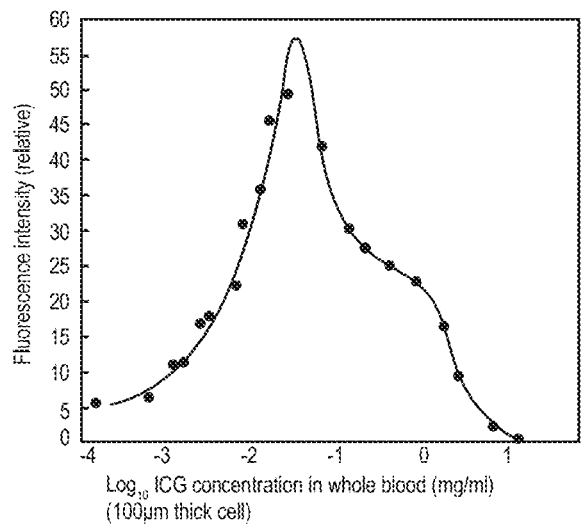
Figure 20B:
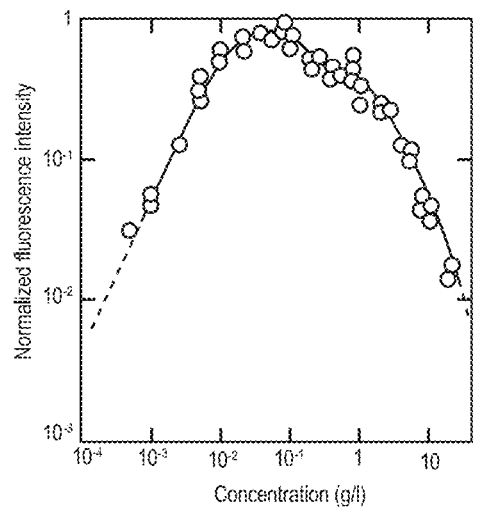
Figure 20C:
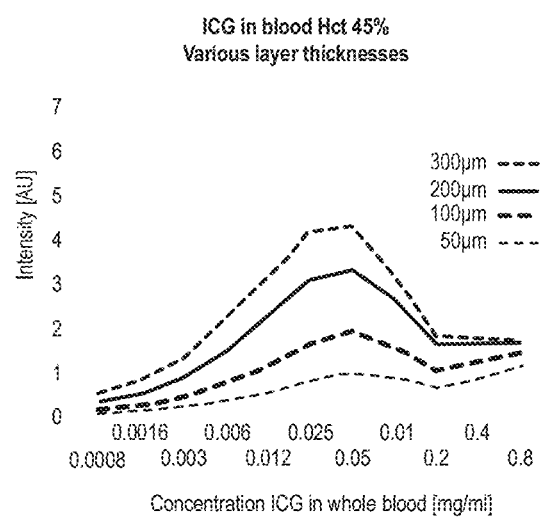
Figure 20D:
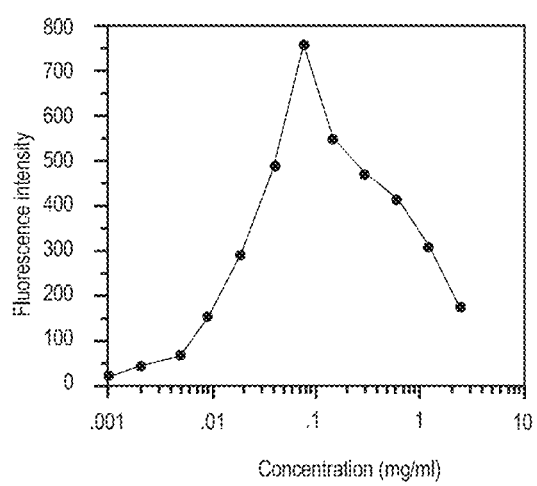

FIGS. 19A and 19B are graphs illustrating the dependence of ICG fluorescence on ICG concentration. In each of FIGS. 19A and 19B, the red line represents single-photon fluorescence results and the black line represents two-photon fluorescence results. The results are graphed in FIG. 19A as a linear scale of fluorescence intensity over nM concentrations of ICG. The results are graphed in FIG. 19B as a logarithmic scale of fluorescence intensity over mg/ml concentrations of ICG.

FIGS. 20A-20D are graphs illustrating prior art examples of the nonlinear dependency of ICG fluorescence over concentration.

Figure 21:
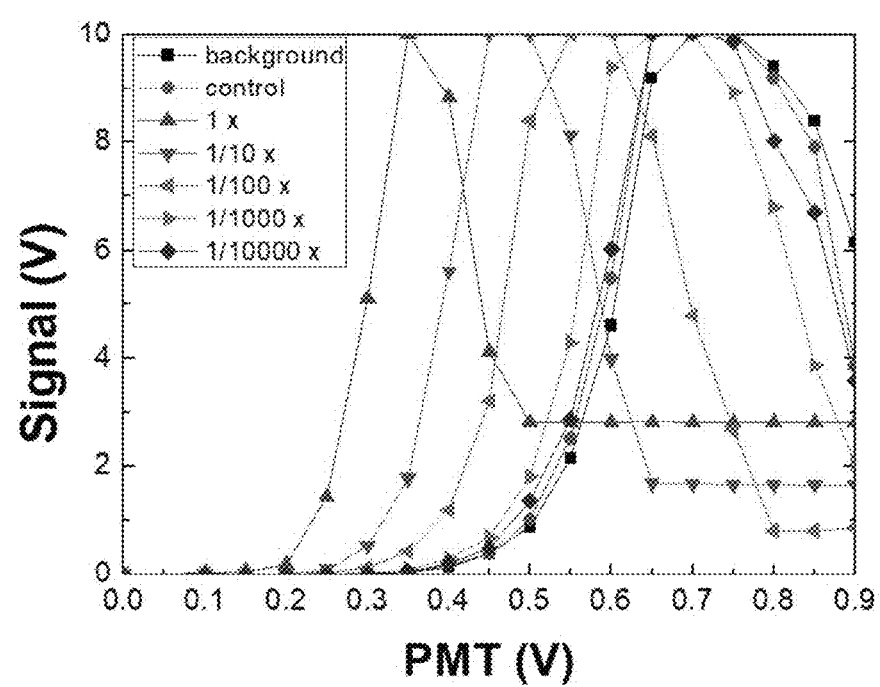

FIG. 21 is a graph illustrating signals of ICG fluorescence at different concentrations over a photomultiplier (PMT) voltage range.

Figure 22A:
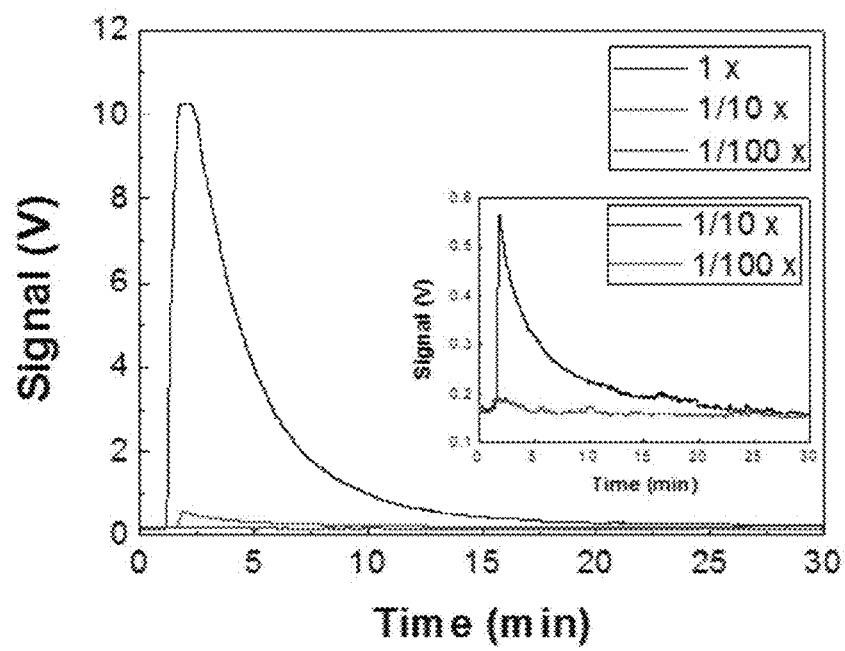

FIG. 22A is a graph of the fluorescence dosimetry curves of ICG injected at 1×, ⅒×, and ¹⁄₁₀₀× of the clinical dosage, measured at 0.4 V PMT bias. The inset graph of FIG. 22A illustrates a zoomed view of the ⅒× and ¹⁄₁₀₀× data.

Figure 22B:
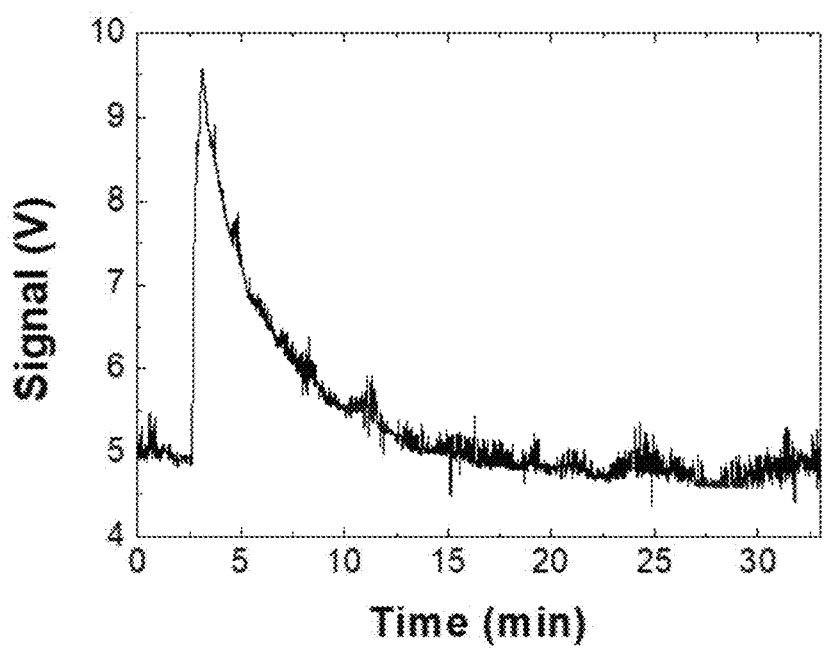

FIG. 22B is a graph of the fluorescence dosimetry curve after injection of ¹⁄₁₀₀× of the clinical dosage of ICG, measured at 0.58 V PMT bias.

DETAILED DESCRIPTION

Before describing various embodiments of the present disclosure in detail, it is to be understood that this disclosure is not limited to the parameters of the particularly exemplified systems, methods, apparatus, products, processes, and/or kits, which may, of course, vary. Thus, while certain embodiments of the present disclosure will be described in detail, with reference to specific configurations, parameters, components, elements, etc., the descriptions are illustrative and are not to be construed as limiting the scope of the claimed invention. In addition, the terminology used herein is for the purpose of describing the embodiments and is not necessarily intended to limit the scope of the claimed invention.

Furthermore, it is understood that for any given component or embodiment described herein, any of the possible candidates or alternatives listed for that component may generally be used individually or in combination with one another, unless implicitly or explicitly understood or stated otherwise. Additionally, it will be understood that any list of such candidates or alternatives is merely illustrative, not limiting, unless implicitly or explicitly understood or stated otherwise.

In addition, unless otherwise indicated, numbers expressing quantities, constituents, distances, or other measurements used in the specification and claims are to be understood as being modified by the term "about," as that term is defined herein. Accordingly, unless indicated to the contrary, the numerical parameters set forth in the specification and attached claims are approximations that may vary depending upon the desired properties sought to be obtained by the subject matter presented herein. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the subject matter presented herein are approximations, the numerical values set forth in the specific examples are reported as precisely as possible. Any numerical values, however, inherently contain certain errors necessarily resulting from the standard deviation found in their respective testing measurements.

Any headings and subheadings used herein are for organizational purposes only and are not meant to be used to limit the scope of the description or the claims.

Overview of Systems and Methods for Detecting Tissue Ischemia and Evaluating Organ Function Using Serum Luminescence As provided above, ischemia-reperfusion damage induced organ failures are major risks associated with organ transplantation. Further, some ischemia (e.g., bowel ischemia or acute mesenteric ischemia) can prove difficult to diagnose owing to a lack of diagnostic symptomology, and late diagnosis of ischemia is associated with a high mortality rate. Early diagnosis can help physicians to prescribe or administer the appropriate therapy (e.g., anticoagulants for deep vein thrombosis) and save patients' lives. Accordingly, systems and methods are needed to develop a sensitive assay to screen for ischemia and/or infarctions within organs, particularly at an early stage.

Systems and methods of the present disclosure utilize serum luminescence and its spectroscopic features for the early sensing of tissue ischemia and shock conditions in organs. The stress factors and radicals produced at sites of ischemia are diffused and released systemically through the circulatory system, thus altering the photophysical or photochemical properties of blood. As implemented in the disclosed systems and methods, monitoring of blood luminescence can quickly and sensitively reflect the circulation microenvironment in a timely manner to provide actionable insights into the presence of ischemia or potential organ dysfunction. Embodiments disclosed herein can bridge the diagnostic gap between sensitive symptom diagnoses (e.g., physiologic monitoring) and specific marker-based diagnoses (e.g., diagnostic protein markers), resulting in an effective early screening modality.

Oxidative stress and/or cellular damage in tissues caused by ischemia/infarction can cause the release of signaling molecules (e.g., cytokines and chemokines) or radicals into the blood stream—whether directly or indirectly through the induction of gene expression changes in the surrounding tissue via the activation or release of transcription factors. The burst of biochemical factors can cause a perturbation within the physiology of blood cells, endothelial cells, and the change of chemical and physical microenvironment in serum. These factors may enhance, quench, or alter the luminescence properties of cells and plasma and/or may alter the chromatography features of these fluorophores.

In a first embodiment, the systems and methods of the present disclosure enable the detection of ischemia/infarction induced perturbations in the chemical and physical microenvironment of serum using the luminescence properties of endogenous chromophores in serum and/or plasma. Compared to in vitro diagnosis of protein hallmarks, luminescence spectroscopy can selectively excite and sensitively detect various serum chromophores at trace amount and routinely monitor the change on demand. Advantageously, luminescence spectroscopy also does not require expensive antibodies for quantitative assay, which is convenient for on-site screening, and when combined with the assay of protein hallmarks, the types and locations of ischemia/infarction can be further confirmed.

In a second embodiment, the systems and methods of the present disclosure enable the detection of organ dysfunction using luminescent dosimetry of endogenous or intravenously administered chromophores. The chromophores may associate with plasma proteins right after intravenous administration, and this chromophore-protein complex will be metabolized by certain organs, allowing the retention rate of the chromophore-protein complex to be used as a surrogate marker to reflect organ function. For example, FDA approved ICG can associate with serum albumins and be specifically metabolized by the liver. Accordingly, the retention percentage at 15-minutes post ICG injection (ICG-15) can be used as a diagnostic index for the evaluation of liver function. Normally, the ICG-15 is below 10% of the initial concentration for a healthy person. On the other hand, if the liver function of a hepatocellular carcinoma patient is poor, as measured by the ICG-15 being higher than 40%, then the patient is not eligible for a hepatectomy. When kidney failure occurs, the albumin-ICG complex may not be completely processed by the kidney, allowing the chromophore-protein complex to pass into the bladder, thereby causing the ICG-15 value to be lower than that expected from normal metabolism by fully functioning organs.

Endogenous chromophores like bilirubin can associate with albumin and may be used instead of ICG to evaluate the liver function and/or detect kidney failure. For example, individuals who have poor liver function typically present with jaundice, which is the result of poor bilirubin metabolism by hepatocytes. Such retention dosimetry of foreign/endogenous chromophores in serum can be used to measure or monitor organ function and detect failure of the organ.

Systems and methods of the present disclosure utilize sensitive photodetectors like photomultiplier tubes to detect weak luminescence signals, and by intentionally selecting the far red or near infrared chromophores, the disclosed systems and methods mitigate background interference from tissues. For example, ICG can be excited at 780 nm and emit fluorescence longer than 810 nm, and bilirubin can be excited at 785 nm and luminesce between 800-850 nm. These wavelengths are much longer than the background autofluorescence of porphyrins (600-750 nm). The systems and methods of the present disclosure implement luminescence dosimetry to evaluate the circulated chromophores at trace amounts, greatly reducing the required dosage of exogenous chromophores for accurate and reliable evaluation of organ function. As a result, the disclosed systems and methods can beneficially reduce patient exposure and toxicity to exogenous chromophores, and because a lower concentration of chromophores can be used, the costs associated with implementation can also be reduced.

As used herein, the term "endogenous chromophore" is intended to include at least reduced nicotinamide adenine dinucleotide (NADH), flavin adenine dinucleotide (FAD), flavin mononucleotide (FMN), riboflavin, or other flavins, bilirubin, biliverdin, and porphyrins but may additionally include other endogenous chromophores. It should be appreciated that aggregated forms of molecules may have different features of spectroscopy. Further, the exogenous chromophores disclosed herein for retention dosimetry include, but are not limited to, indocyanine green (ICG), fluorescein, and methylene blue.

In general, the embodiments disclosed herein can non-invasively (e.g., transdermally) monitor serum or plasma luminescence at anatomical locations having fewer pigments and a rich networks of vessels. For example, anatomical locations such as the mucosa on the lips, nail folds, or ear lobules are generally suitable for transdermal luminescence measurements. An objective lens can be used for efficient light excitation and luminescence collection, and to maximize the stability of signal acquisition, systems and methods of the present disclosure can include a tissue mount to fix the axial distance between vessel networks and the focusing lens. A tissue mount could be, for example, a metallic ring with air suction channels, so that tissues can be attached to the ring by applying a negative pressure in the air suction channels. Additionally, or alternatively, the access ports from central venous/artery catheters, commonly used in intensive care or surgery, can be used to collect serum and make routine measurement of luminescence. When available, use of the access ports can result in a better signal to noise ratio. In some embodiments, an adaptor can be designed to fit the luminescence measurement apparatus and can include, for example, the transparent port or branches on the parts of central venous/artery catheters. In some embodiments, a sterilized device for separating serum from blood cells, like a microfluidic chip, can be used.

It should be further appreciated that collected luminescence can be separated from excitation light using a beam-splitter, and the residual excitation light can be further blocked by one or more filters, such as a long-pass or short-pass filter, depending on the excitation mechanisms—single photon excitation typically use long-pass filters, while multiphoton excitation typically use short-pass filters—as known in the art. Further, conversion of the acquired luminescence signal to electric signals can be implemented by, for example, photomultiplier tubes, CCD detectors, or avalanche photo diodes with the signals being recorded by analogue devices or digital data-sampling cards, as known in the art.

If required, a light scanning module, containing scanning mirrors and lenses, can be used to steer the excitation beam and search for the location of blood vessels. Since tissues without vessels do not provide luminescence of serum chromophores, a scanning paradigm (e.g., line scanning or circular contour scanning) can be used to identify the location of vessels followed by signal verification to ensure the signal originated from serum. Advantageously, the luminescence from serum will be frequently blocked by red blood cells, allowing the extraction of the component of luminescence signal from vessels in frequency or speckle domain.

Systems and Methods for Detecting Acute Organ Ischemia Using Luminescence Spectroscopy Embodiments of the present disclosure enable the detection of acute organ ischemia, including, for example, the detection of acute mesenteric ischemia, from serum fluorescence.

For the diagnosis of tissue ischemia, physicians need to confirm both the actual occurrence of ischemia as well as the anatomical location of the ischemia. The first part relies on patients' symptoms, physiological signs, profiles of blood tests, or imaging examination. The second part relies on the companion diagnosis with organ-specific protein markers. However, it is often the case that the symptomology is too vague in the early stages of ischemia or shock to properly diagnose ischemia. Blood test usually take time to generate reports and often require medical experts to interpret the test data. These constraints and limitation of diagnostic resources are often the cause of late diagnosis of ischemia and consequently results in an increase in the mortality of patients.

The systems and methods disclosed herein provide a sensitive and quick screening tool that can be implemented on-site to monitor and detect early-stage ischemic conditions. Following the detection of ischemia, protein markers can be used to specifically identify the location of ischemia or organ infarction. It should be appreciated that although the disclosed systems and methods are exemplified using an acute mesenteric ischemia model and fluorescence spectroscopy to demonstrate the feasibility of this idea, other ischemia can be detected using the same or similar system architectures and/or methodologies within mammals, generally, preferably within humans.

In one embodiment, a method for detecting tissue ischemia within a mammal (e.g., a rat) includes (i) isolating serum from a blood sample, (ii) directing an excitation light at the serum, (iii) receiving an endogenous serum chromophore emission light from the excited serum, and (iv) determining a presence of an ischemic condition based on an intensity of the endogenous serum chromophore emission light.

The step of isolating serum can include, for example, serial centrifugation of a blood sample to obtain a final supernatant comprising the non-cellular, liquid fraction of the blood sample. It should be appreciated that the serum sample may include clotting components if an anticoagulant is used to store the blood sample prior to processing and may, in some cases, be more properly defined as blood plasma. Nevertheless, for the purposes of the present disclosure, the terms "serum" and "blood plasma" are understood to be functionally interchangeable.

Alternatively, serum can be isolated from the blood sample by other means, including, for example, by routing (e.g., continuously or in batch) blood through a microfluidic chip, or similar device, configured to separate the serum from the blood. In one embodiment, the microfluidic chip can be coupled to the transparent port or branch part of a central venous/artery catheter where it continuously separates serum from blood routed therethrough.

The step of directing excitation light at the serum can include generating excitation light from any concentrated light source, such as a continuous wave laser. Preferably, the excitation light is configured to produce an excitation wavelength between about 440-480 nm, more preferably about 480 nm.

The step of receiving the endogenous serum chromophore emission light from the excited serum can be performed by an objective lens and/or photodetector positioned to receive the luminescence signals from the endogenous chromophore. In some instances, the serum is excited on a microscope slide or multi-well sample plate positioned within the optical axis of an imaging system (e.g., a high content imaging system, fluorescence microscope, or similar). Alternatively, the excited serum can be positioned within the optical axis of an objective lens and/or photodetector of an imaging system configured for real time monitoring of serum chromophore luminescence. Such an imaging system can include, among other things, a mount associated with the objective lens that is configured to fix an axial distance between the serum source and the objective lens. The serum source can be an anatomical location having fewer pigments and a rich network of blood vessels, such as the mucosa on the lips, nail folds, and ear lobules, or any other anatomical location that is generally suitable for transdermal luminescence measurements. When associated with an anatomical location, the mount may constitute a tissue mount having a tissue attachment mechanism for anchoring the tissue mount. As a non-limiting example, the tissue mount may include an air suction channel configured to pull a negative pressure at or near the target area.

In some instances, the mount is indirectly associated with an anatomical location and may include an adaptor. For example, the serum source may be a transparent port or branch part of a central venous/artery catheter (or microfluidic device associated therewith, as described above), and the mount associates directly with the transparent port or branch part directly, or indirectly through an adaptor associated therewith, to fix the axial distance between the serum source and the objective lens/photodetector.

The endogenous serum chromophore emission light received from the excited serum may be captured at a single photon spectrometer and may have an emission wavelength between about 500-550 nm, preferably between about 510-540 nm, more preferably between about 515-525 nm, or in some instances, about 520 nm. In some embodiments, the disclosed methods for determining a presence of an ischemia may additionally include normalizing the intensity of the endogenous serum chromophore emission light to about 654 nm and measuring a peak fluorescence intensity between about 510-530 nm, preferably about 517 nm.

Referring back to the exemplary method, the step of determining a presence of an ischemic condition based on an intensity of the endogenous serum chromophore emission light can include calculating an optical index. The optical index comprises an arithmetic calculation of spectral intensities at a plurality of wavelengths that are each associated with a principle chromophore component, determined from an excitation wavelength swept fluorescence spectra of the blood sample. In some instances, the optical index is a ratio of 517 nm/556 nm light intensity values and/or 517 nm/654 nm light intensity values, and if the optical index has a peak intensity disparity at 920 nm, the ischemic condition is determined to be present while if the optical index does not have a peak intensity disparity at 920 nm, the ischemic condition is determined not to be present.

The transformed data obtained from determining the presence of an ischemic condition can be used to inform actionable patient treatment and/or medical intervention steps. In one embodiment, the method includes conducting an in vitro assay of serum marker proteins to confirm a type and/or anatomical location of the tissue ischemia if the ischemia is present, and if the ischemic condition is not present, the method includes continued monitoring of the endogenous serum chromophore emission light of serum isolated at later timepoints. The method may additionally include administering one or more pharmaceutical compositions, such as an anti-coagulant or clot breaking therapeutic (e.g., heparin), or other situation-dependent therapy.

In some embodiments, the step of determining a presence of an ischemic condition based on an intensity of the endogenous serum chromophore emission light can include comparing the intensity of the endogenous serum chromophore emission light to a baseline emission intensity. A baseline emission intensity having a lower value than the intensity of the endogenous serum chromophore emission light can be indicative of an ischemic condition. In some instances, the baseline emission intensity is a threshold emission intensity, an emission light intensity value associated with a first (or earlier) timepoint, or a predetermined value associated with a non-ischemic condition. For example, serum can be isolated at a catheter for repeated or constant measurements of the intensity of the endogenous serum chromophores, and the presence of an ischemic condition can be determined by identifying an intensity of the endogenous serum chromophore that has exceeded a threshold intensity level.

Systems and Methods for Detecting Organ Dysfunction Using Luminescence Dosimetry Embodiments of the present disclosure additionally enable the detection of organ dysfunction using luminescence dosimetry.

An exemplary method of detecting organ dysfunction can include optionally administering to a mammal, preferably a human, a trace amount of an exogenous chromophore. When administered, it is preferable that the exogenous chromophore is received into and processed from the circulatory system of the mammal. For example, the trace amount of exogenous chromophore can be administered intravenously and can include one or more of indocyanine green (ICG), fluorescein, or methylene blue. In one embodiment, the trace amount of exogenous chromophore is ICG and is administered to an in vivo concentration at or below about $10^{-3}$ mg/mL, preferably to an in vivo concentration of ICG between about $10^{-4}$ mg/mL to about $10^{-7}$ mg/mL.

The exemplary method can additionally include identifying a blood vessel within the mammal. As above, the methods for detecting organ dysfunction may favor identifying blood vessels at anatomical locations having fewer pigments and a rich network of blood vessels, such as the mucosa on the lips, nail folds, and ear lobules, or any other anatomical location that is generally suitable for transdermal luminescence measurements. Accordingly, this step, in addition to other steps and methods for detecting organ dysfunction within a mammal, can be implemented using the non-invasive serum luminescence systems described above. Such a system may automatically identify the blood vessel within the target area using a line scanning or circular contour scanning module. The scanning module can include scanning mirrors and lenses configured to steer the excitation light within the target area. In some embodiments, the blood vessel is identified using THG imaging. Additionally, or alternatively, the blood vessel is identified via two photon fluoroscopy using a transmitted excitation light having an excitation wavelength of greater than about 900 nm with the transdermal measurement being obtained at an emission wavelength of less than about 900 nm.

The method can additionally include transmitting excitation light to luminal contents of the blood vessel comprising the exogenous chromophore and obtaining a transdermal measurement of the exogenous chromophore. As above, a laser or other excitation light source may be used to excite the luminal contents of the blood vessel, and an objective lens and/or photodetector can be used to capture the transdermal measurement of the exogenous chromophore. In one embodiment, a two-photon fluorescent microscopy system is used. In such an embodiment, the serum can be excited via two-photon absorption having an excitation wavelength between about 800-1040 nm, preferably between about 920-980 nm, more preferably about 920 nm. In some embodiments, particularly when ICG is being used as the exogenous chromophore, a suitable operation bias voltage for obtaining a transdermal measurement of the exogenous chromophore is between 0.4-0.6 V.

Methods for detecting organ dysfunction can additionally include the step of determining organ dysfunction based on the transdermal luminescence measurement. In some embodiments, determining organ dysfunction based on the transdermal luminescence measurement includes comparing the transdermal luminescence measurement to a healthy, expected luminescence measurement calculated from a known chromophore decay constant and based on an amount of time following administration of the solution. In some embodiments, the transdermal luminescence measurements are used to determine a patient-specific dosimetry curve, which can be compared to a known dosimetry curve for a healthy individual or from an individual having a non-dysfunctional organ. For example, if the patient-specific dosimetry curve indicates the chromophore-protein complex is being metabolized at a normal rate, it is unlikely that the liver or kidney are dysfunctional. On the other hand, if the patient-specific dosimetry curve indicates a slower rate of metabolizing the chromophore-protein complex than would be expected, the patient is likely to have a liver dysfunction, whereas if the patient-specific dosimetry curve indicates a faster rate of metabolizing the chromophore-protein complex than would be expected, the patient is likely to have a dysfunction.

Similar to the methods for determining the presence of an ischemic condition, the transformed data obtained from the methods for detecting organ dysfunction can be used to inform actionable patient treatment and/or medical intervention steps. In one embodiment, the method includes conducting an in vitro assay of serum marker proteins to confirm a type and/or anatomical location of organ dysfunction, and if the organ is dysfunctional, the method can include continued administering (or cease administering) one or more pharmaceutical compositions and/or implementing one or more organ-specific treatment regimens to salvage, rescue, or replace the dysfunctional organ.

Computer Systems of the Present Disclosure

In some embodiments, some of the steps within the foregoing methods and/or components of the associated systems may be controlled by or include a computer system. Such computer systems can include one or more processors and one or more hardware storage devices having stored thereon computer-executable instructions that, when executed by at least one of the one or more processors, configure the computer system to perform one or more acts. For example, the computer system can be configured to direct the excitation light to excite the endogenous and/or exogenous chromophore, automatically identify the one or more blood vessels within the target area using a line scanning or circular contour scanning module comprising scanning mirrors and lenses configured to steer the excitation light within the target area, receive luminescence signals at the photodetector electronically coupled to the computer system and positioned in an emission light path of the objective lens, and/or determine a presence of tissue ischemia and/or liver dysfunction based on the luminescence signals.

The computer-executable instructions may additionally cause the computer system to calculate an optical index and/or dosimetry curve based on the luminescence signals received at the photodetector. The computer-executable instructions may additionally cause the computer system to calculate and compare the dosimetry curve to a standard decay constant of the exogenous chromophore within a healthy mammal to inform the determination of organ dysfunction. It should be appreciated that other desired functionalities or automations of the disclosed systems may be implemented on a computer system.

It will be further appreciated that computer systems are increasingly taking a wide variety of forms. In this description and in the claims, the term "computer system" or "computing system" is defined broadly as including any device or system—or combination thereof—that includes at least one physical and tangible processor and a physical and tangible memory capable of having thereon computer-executable instructions that may be executed by a processor. By way of example, not limitation, the term "computer system" or "computing system," as used herein is intended to include personal computers, desktop computers, laptop computers, tablets, hand-held devices (e.g., mobile telephones, PDAs, pagers), microprocessor-based or programmable consumer electronics, minicomputers, mainframe computers, multi-processor systems, network PCs, distributed computing systems, datacenters, message processors, routers, switches, and even devices that conventionally have not been considered a computing system, such as wearables (e.g., glasses).

The memory may take any form and may depend on the nature and form of the computing system. The memory can be physical system memory, which includes volatile memory, non-volatile memory, or some combination of the two. The term "memory" may also be used herein to refer to non-volatile mass storage such as physical storage media.

The computing system also has thereon multiple structures often referred to as an "executable component." For instance, the memory of a computing system can include an executable component. The term "executable component" is the name for a structure that is well understood to one of ordinary skill in the art in the field of computing as being a structure that can be software, hardware, or a combination thereof.

For instance, when implemented in software, one of ordinary skill in the art would understand that the structure of an executable component may include software objects, routines, methods, and so forth, that may be executed by one or more processors on the computing system, whether such an executable component exists in the heap of a computing system, or whether the executable component exists on computer-readable storage media. The structure of the executable component exists on a computer-readable medium in such a form that it is operable, when executed by one or more processors of the computing system, to cause the computing system to perform one or more functions, such as the functions and methods described herein. Such a structure may be computer-readable directly by a processor—as is the case if the executable component were binary. Alternatively, the structure may be structured to be interpretable and/or compiled—whether in a single stage or in multiple stages—so as to generate such binary that is directly interpretable by a processor.

The term "executable component" is also well understood by one of ordinary skill as including structures that are implemented exclusively or near-exclusively in hardware logic components, such as within a field programmable gate array (FPGA), an application specific integrated circuit (ASIC), Program-specific Standard Products (ASSPs), System-on-a-chip systems (SOCs), Complex Programmable Logic Devices (CPLDs), or any other specialized circuit. Accordingly, the term "executable component" is a term for a structure that is well understood by those of ordinary skill in the art of computing, whether implemented in software, hardware, or a combination thereof.

The terms "component," "service," "engine," "module," "control," "generator," or the like may also be used in this description. As used in this description and in this case, these terms—whether expressed with or without a modifying clause—are also intended to be synonymous with the term "executable component" and thus also have a structure that is well understood by those of ordinary skill in the art of computing.

While not all computing systems require a user interface, in some embodiments a computing system includes a user interface for use in communicating information from/to a user. The user interface may include output mechanisms as well as input mechanisms. The principles described herein are not limited to the precise output mechanisms or input mechanisms as such will depend on the nature of the device. However, output mechanisms might include, for instance, speakers, displays, tactile output, projections, holograms, and so forth. Examples of input mechanisms might include, for instance, microphones, touchscreens, projections, holograms, cameras, keyboards, stylus, mouse, or other pointer input, sensors of any type, and so forth.

Accordingly, embodiments described herein may comprise or utilize a special purpose or general-purpose computing system. Embodiments described herein also include physical and other computer-readable media for carrying or storing computer-executable instructions and/or data structures. Such computer-readable media can be any available media that can be accessed by a general purpose or special purpose computing system. Computer-readable media that store computer-executable instructions are physical storage media. Computer-readable media that carry computer-executable instructions are transmission media. Thus, by way of example—not limitation—embodiments disclosed or envisioned herein can comprise at least two distinctly different kinds of computer-readable media: storage media and transmission media.

Computer-readable storage media include RAM, ROM, EEPROM, solid state drives ("SSDs"), flash memory, phase-change memory ("PCM"), CD-ROM or other optical disk storage, magnetic disk storage or other magnetic storage devices, or any other physical and tangible storage medium that can be used to store desired program code in the form of computer-executable instructions or data structures and that can be accessed and executed by a general purpose or special purpose computing system to implement the disclosed functionality of the invention. For example, computer-executable instructions may be embodied on one or more computer-readable storage media to form a computer program product.

Transmission media can include a network and/or data links that can be used to carry desired program code in the form of computer-executable instructions or data structures and that can be accessed and executed by a general purpose or special purpose computing system. Combinations of the above should also be included within the scope of computer-readable media.

Further, upon reaching various computing system components, program code in the form of computer-executable instructions or data structures can be transferred automatically from transmission media to storage media (or vice versa). For example, computer-executable instructions or data structures received over a network or data link can be buffered in RAM within a network interface module (e.g., a "NIC") and then eventually transferred to computing system RAM and/or to less volatile storage media at a computing system. Thus, it should be understood that storage media can be included in computing system components that also—or even primarily—utilize transmission media.

Those skilled in the art will further appreciate that a computing system may also contain communication channels that allow the computing system to communicate with other computing systems over, for example, a network. Accordingly, the methods described herein may be practiced in network computing environments with many types of computing systems and computing system configurations. The disclosed methods may also be practiced in distributed system environments where local and/or remote computing systems, which are linked through a network (either by hardwired data links, wireless data links, or by a combination of hardwired and wireless data links), both perform tasks. In a distributed system environment, the processing, memory, and/or storage capability may be distributed as well.

Those skilled in the art will also appreciate that the disclosed methods may be practiced in a cloud computing environment. Cloud computing environments may be distributed, although this is not required. When distributed, cloud computing environments may be distributed internationally within an organization and/or have components possessed across multiple organizations. In this description and the following claims, "cloud computing" is defined as a model for enabling on-demand network access to a shared pool of configurable computing resources (e.g., networks, servers, storage, applications, and services). The definition of "cloud computing" is not limited to any of the other numerous advantages that can be obtained from such a model when properly deployed.

A cloud-computing model can be composed of various characteristics, such as on-demand self-service, broad network access, resource pooling, rapid elasticity, measured service, and so forth. A cloud-computing model may also come in the form of various service models such as, for example, Software as a Service ("SaaS"), Platform as a Service ("PaaS"), and Infrastructure as a Service ("IaaS"). The cloud-computing model may also be deployed using different deployment models such as private cloud, community cloud, public cloud, hybrid cloud, and so forth.

Although the subject matter described herein is provided in language specific to structural features and/or methodological acts, it is to be understood that the subject matter defined in the appended claims is not necessarily limited to the described features or acts so described. Rather, the described features and acts are disclosed as example forms of implementing the claims.

Abbreviated List of Defined Terms

To assist in understanding the scope and content of the foregoing and forthcoming written description and appended claims, a select few terms are defined directly below.

The terms "about," "approximately," and "substantially," as used herein, represent an amount or condition close to the stated amount or condition that still performs a desired function or achieves a desired result. For example, the terms "about," "approximately," and "substantially" may refer to an amount or condition that deviates by less than 10%, or by less than 5%, or by less than 1%, or by less than 0.1%, or by less than 0.01% from a stated amount or condition.

As used herein, the terms "blood plasma" and "serum" are to be understood as functionally interchangeable and are meant to describe the liquid, non-cellular portion of blood.

The term "healthcare provider," as used herein, generally refers to any licensed and/or trained person prescribing, administering, or overseeing the diagnosis and/or treatment of a patient or who otherwise tends to the wellness of a patient. This term may, when contextually appropriate, include any licensed medical professional, such as a physician, a physician's assistant, a nurse, a nurse practitioner, a phlebotomist, a veterinarian, etc.

As used herein, the term "luminescence property" or "luminescence properties" include, but are not limited to, fluorescence spectra, fluorescence excitation spectra, fluorescence/phosphorescence lifetime, and fluorescence based ultra-/high-performance liquid chromatography tandem mass spectra.

The term "patient" generally refers to any animal, for example a mammal, under the care of a healthcare provider, as that term is defined herein, with particular reference to humans under the care of a physician or other relevant medical professional. For the purpose of the present application, a "patient" may be interchangeable with an "individual" or "person." In some embodiments, the individual is a human patient.

The term "physician," as used herein, generally refers to a medical doctor or similar licensed healthcare provider specialized medical doctor performing biopsies. This term may, when contextually appropriate, include any other medical professional, including any licensed medical professional or other healthcare provider, such as a physician's assistant, a nurse, a veterinarian (such as, for example, when the patient is a non-human animal), etc.

As used herein, the term "real time" is understood to mean a present temporal occurrence. For example, an event is occurring in "real time" when an observation of the event occurs contemporaneously with the occurrence of the event. Additionally, real time calculations or determinations include those calculations or determinations that are being made based on data obtained contemporaneously with the measurement or receipt of the associated data. For clarity, contemporaneous events or actions are those that are coincident in time—that is, their occurrence is separated by no more than an hour, preferably by no more than 10 minutes, and more preferably by no more than 1 minute.

Unless defined otherwise, all technical and scientific terms used herein have the same meaning as commonly understood by one of ordinary skill in the art to which the present disclosure pertains.

Various aspects of the present disclosure, including devices, systems, and methods may be illustrated with reference to one or more embodiments or implementations, which are exemplary in nature. As used herein, the term "exemplary" means "serving as an example, instance, or illustration," and should not necessarily be construed as preferred or advantageous over other embodiments disclosed herein. In addition, reference to an "implementation" of the present disclosure or invention includes a specific reference to one or more embodiments thereof, and vice versa, and is intended to provide illustrative examples without limiting the scope of the invention, which is indicated by the appended claims rather than by the following description.

As used throughout this application the words "can" and "may" are used in a permissive sense (i.e., meaning having the potential to), rather than the mandatory sense (i.e., meaning must). Additionally, the terms "including," "having," "involving," "containing," "characterized by," as well as variants thereof (e.g., "includes," "has," "involves," "contains," etc.), and similar terms as used herein, including within the claims, shall be inclusive and/or open-ended, shall have the same meaning as the word "comprising" and variants thereof (e.g., "comprise" and "comprises"), and do not exclude additional un-recited elements or method steps, illustratively.

It will be noted that, as used in this specification and the appended claims, the singular forms "a," "an" and "the" include plural referents unless the context clearly dictates otherwise. Thus, for example, reference to a singular referent (e.g., "widget") includes one, two, or more referents. Similarly, reference to a plurality of referents should be interpreted as comprising a single referent and/or a plurality of referents unless the content and/or context clearly dictate otherwise. For example, reference to referents in the plural form (e.g., "widgets") does not necessarily require a plurality of such referents. Instead, it will be appreciated that independent of the inferred number of referents, one or more referents are contemplated herein unless stated otherwise.

EXAMPLES

Example 1

Methods for detecting tissue ischemia, as provided herein, were validated using a rat model of mesenteric ischemia. Referring now to FIG. 1, the absorption spectra of water and rat serum at 0-, 5-, 20-, and 45-minutes poste mesenteric ischemia are shown. Briefly, rat serum was obtained from male Wistar rats aged between 7 and 9 weeks with a mass of 250-300 g that were subjected to a model of mesenteric ischemia. Rats were initially anesthetized with gas and the fistula at the rats' carotid artery was grafted. The rats' abdominal cavity was opened, and prior to using two clips to clip the superior mesenteric artery (SMA), a "baseline" blood sample was collected from the fistula. The SMA was then clipped to stop the blood flow to the intestines, thereby simulating human mesenteric ischemia in the rat model.

Blood samples were collected at different ischemic time points, and blood was reperfused in the SMA at the end of the ischemia stage by removing the clips. After reperfusion, we also collected reperfusion blood samples at different time points.

Isolated blood samples were stored in tubes with heparin for anticoagulation. A refrigerated centrifuge was then used to separate blood samples using an initial centrifugation protocol of 500×g for 5 minutes at 10° C. The upper layer supernatant was collected and centrifuged using a subsequent centrifugation protocol of 300×g for 20 minutes at 10° C. The serum samples were then secured for spectroscopy. At least two rats were used for each ischemia timepoint.

A single-photon excited spectrometer and a multi-photon fluorescence imaging system (Zeiss, LSM 710) were used. On the multi-photon fluorescence imaging system, a wavelength tunable Ti:sapphire femtosecond laser (700-1040 nm) was used to excite the rat serum samples dropped on a microscope slide via a 40× NA 1.15 objective. The detected signals were integrated over all scanning pixels and the luminescence intensity was obtained at certain excitation wavelength. The power at different excitation wavelength was equalized so that excitation intensity after the objective was equal.

Since the absorption spectra may be dominated by other substances, the fluorescence spectra of serum was initially determined to identify features specific to ischemia. Referring again to FIG. 1, the absorption spectra of rat serum occurred from 350 nm to 450 nm and from 525 nm to 600 nm.

The fluorescence spectrum of serum sampled from rats that underwent mesenteric ischemia was also determined at baseline (BL) and at 30-, 45-, 60-, and 90-minutes post ischemia. As shown in FIG. 2, the baseline fluorescence level is low prior to ischemia. After ischemia, a yellow fluorescence peak around 520 nm was detected when the serum was excited with a blue light source (440-480 nm).

The fluorescence excitation spectrum shown in FIG. 3 illustrates obvious differences of 520 nm emission yield at about 480 nm between baseline (black curve) and ischemic (brown curve) serum samples. At the wavelength after 450 nm, serum from ischemic rats had a higher 520 nm fluorescence intensity. The excitation wavelength was fixed at 480 nm to selectively excite the ischemia-specific fluorescence. The intensity peak at 520 nm increased within serum samples of later-staged ischemia while the waveforms of serum fluorescence at different ischemia timepoints are roughly the same.

Referring now to FIGS. 4A and 4B, the fluorescence spectra of baseline serum and of serum collected 0-, 5-, 30-, and 45-minutes post ischemia-reperfusion (IR) from two rats were determined to measure the reperfusion dynamics of the yellow fluorescence peak. These rats underwent a reperfusion of blood after 45 minutes of ischemia with serum being isolated from blood samples collected at 0-, 5-, 30-, and 45-minutes post IR. The baseline sample was collected before ischemia. Initially, there was still yellow fluorescence peak at about 520 nm, but as the reperfusion time went by, the intensity of the yellow fluorescence peak decreased. Both rats (i.e., as shown in FIGS. 4A and 4B, respectively) showed a similar trend. The characteristic yellow fluorescence increased with the mesenteric ischemia and decreased after the reperfusion of blood to the mesenteric tissues, indicating a potential diagnostic marker for mesenteric ischemia.

Referring now to FIGS. 5A and 5B, two-photon fluorescence spectra of baseline serum are illustrated. After removing the interfering background, a yellow fluorescence peaked was observed at 520 nm with a red shoulder extending to 700 nm. The fluorescence intensity of baseline samples were evaluated at different wavelengths by tuning the excitation wavelength from 800 nm to 1040 nm. The fluorescence peaks gradually shifted from 520 nm to 556 nm during tuning of the excitation wavelength. The 654 nm red peaks were still there but weaker. These spectral evidences indicate there are at least three types of yellow and red fluorophores within baseline serum.

Two-photon fluorescence spectra of mesenteric ischemia (FIGS. 6A and 6B) and ischemia-reperfusion rats (FIGS. 7A and 7B) at different excitation wavelengths (tuning from 800-1040 nm) and at the same excitation power show a main peak at about 520 nm. Aside from 520 nm peak, there are other peaks at about 556 nm and 654 nm. Using an excitation wavelength between 800-860 nm results in wider spectrum because more fluorescent substances, emitting from 420-500 nm, are likely excited. This short wavelength component also appeared in baseline serum while showing no appreciable difference in ischemia serum samples.

As mentioned above, fluorescence peaks at 517 nm, 556 nm, and 654 nm all appeared in three conditions: baseline (BL), ischemia only (IS), and ischemia-reperfusion (IR). However, there are still subtle difference among them. At the same 920 nm excitation wavelength, if the spectral intensity is normalized to that at 654 nm, the fluorescence intensity of the main peak at 517 nm in the condition of ischemia-only was significantly larger than the other two conditions, as shown in FIGS. 8A-8D. With continued reference to FIGS. 8A-8D, the fluorescence intensity of the red shoulder did not appreciably change compared with the 520 nm peak. In addition, the spectrum of ischemia-reperfusion sample is roughly similar to that of baseline after normalization.

To make the signatures specific to ischemia condition more significant, the intensity ratio between fluorescence peaks was quantified. If the concentration of one component is relatively unchanged in ischemia, then it can serve as an internal control to perform the self-calibrated semi-quantification. The intensity of 517 nm was divided by the intensity of 556 nm (as shown in FIGS. 9A-9C) and the intensity of 654 nm (as shown in FIGS. 10A-10C), respectively under different excitation wavelengths. Then, the spectra of relative ratios for each sample could be analyzed. As shown in FIGS. 9A-10C, the trend in the spectra of baseline and ischemia-reperfusion are similar—all of them showed flattened spectra with ratio between 1 to 2. However, the ischemia only samples were obviously different from the other two conditions. There was a characteristic peak around 940 nm for all of three ischemia rats. Comparing the intensity ratio of 517 nm/556 nm and 517 nm/654 nm, the scale of the ratio is higher in the 517 nm/654 nm analysis. A higher ratio was also observed at an excitation range from 920 nm to 980 nm. Accordingly, higher ratio may mean more selective excitation to fluorescent substances specific to mesenteric ischemia.

By the fluorescence spectra and the two-photon fluorescence excitation spectra, the systems and methods of the present disclosure enable an optical index that can distinguish whether there is an ischemic condition and is particularly useful in identifying mesenteric ischemia. The results in this Example illustrate that the autofluorescence intensity of rats' blood serum exhibited a drastic increase at 520 nm during mesenteric ischemia and returned to baseline level gradually during the reperfusion phase. Moreover, the characteristic increase of the autofluorescence intensity ratio of 520 nm/654 nm was specific to ischemia state. This approach opens a new route for early diagnosis of acute mesenteric ischemia, which is simple, fast, safe, and non-invasive. In addition, it would be beneficial as a tool for clinical applications to early diagnose or for ruling out acute mesenteric ischemia. While the results described herein are specific to mesenteric ischemia, it is expected that this approach applies to other organ ischemia as well.

Example 2

Embodiments of the present disclosure enable systems and methods for detecting organ dysfunction and were validated using two optical systems to perform ICG fluorescence dosimetry on rats developing hepatocellular carcinoma (HCC).

One optical system used was a multiphoton microscope, which can non-invasively identify the location of vessels in vivo from sectioning two-photon fluorescence imaging. Time-course dynamics of concentration decay were also analyzed by the signal intensity within vessels. The other tested optical system was a point excitation and time course measurement using a 785 nm laser. The results demonstrate that ICG fluorescence dosimetry can reflect the disorder of at least liver function with the development of HCC and likely extends to the detection of other organ dysfunctions.

As shown in the diagram of FIG. 11, the multiphoton microscopy system used the scanning inverted microscope system of Leica DMI 3000M. The laser source was the femtosecond Cr:forsterite laser with a central wavelength of about 1250 nm. The output power was about 570 mW, and the beam diameter was about 2.5 mm. The excited light passed through a set of Galilean telescopes consisting of flat convex lenses and flat concave lenses to shrink the beam size down below 2 mm. Then, the excited beam passed through the periscope to rotate the polarization. After passing through the Iris Pair for system alignment, the beam entered a scanning module composed of a 16 kHz resonant mirror and a galvanometer mirror. The scanning angle of the resonant scanner was 5 degrees. The excited light was expanded by a set of relaying lenses so that it just filled the back aperture of the objective lens. The excitation beam was reflected by a 900-nm edged dichroic beam splitter (DM 900 SP) and focused by an objective lens (63×/NA 1.15. Zeiss) to excite biological tissues.

The generated two-photon fluorescence signals of ICG were epi-collected by the same objective lens and penetrated the DM900 SP. The signals were directed to a 484 nm edged dichroic beam splitter (DM484LP). The third harmonic generation signal (417 nm) was separated from the fluorescent signals longer than 484 nm. The third harmonic generation (THG) and two photon fluorescent (TPF) signals were filtered by a 414 nm/18 nm band pass filter and a 650 nm long pass filter, respectively. These signals were subsequently detected by photomultiplier tubes and digitized by a field programmable logic gate array (FPGA).

Referring now to FIG. 12, the point excitation measurement system included a laser source, optical parts, and a detection/record units. The laser source was a 785 nm continuous wave laser capable of exciting ICG fluorescence through a single-photon process. A fluorescence microscope structure was used to enhance the excitation and collection efficiency of ICG fluorescence. An 801 nm edged dichroic beam splitter was used to reflect excitation beam while passing the ICG fluorescence. The laser beam was focused by a lens onto the vessel of rat ear, as shown in FIG. 13. Then, a set of band pass, notch, and long pass filters were used to block residual laser light. Eventually, the filtered ICG fluorescence was received by a photomultiplier tube and converted into a current signal. The current output of a photomultiplier was sampled by a data recorder and then presented on at a computer system.

The ultrasonic instrument used in this Example was the Prospect small animal 20 MHz ultrasound real-time image system with a 30 microns spatial resolution. The abdominal ultrasound mode B was used, which generates a 2D grayscale image. In addition, the adjustable parameters were fixed as follows: start of depth: 3.7 mm; intensity: 46-50 dB; gain: −4-0 dB.

Hepatocellular carcinoma (HCC) is a well-known malignant liver tumor often caused by liver cirrhosis. N-Nitrosodiethylamine (NDMA, DEN), which is a toxic substance with strong liver toxicity, was used to induce HCC in a rat tumor model. The dose of 300 g rats was 0.75 ml DEN/5 liters in drinking water; the dose of 400 g rats was 1.0 ml DEN/5 liters in drinking water. When the rats weighed over 200 g (about 6-7 weeks), they started to be fed. Group 1 was fed a half dose DEN, while Group 3 was fed a full dose. After 6 weeks of consecutive feeding (at the 12th week of experiment), feeding DEN to Group 1 discontinued. Group 3 continued scheduled DEN feedings for three additional weeks. Liver tumors were formed and confirmed by high-frequency ultrasonic imaging in vivo.

After rats were sacrificed, blood was collected and centrifuged, and the serum from centrifuge was tested, which included albumin, total bilirubin, glutamic pyruvic transaminase and glutamic oxaloacetic transaminase. If the liver is abnormal, the albumin content in the blood will decrease. Total bilirubin contains direct bilirubin and indirect bilirubin, which are the product of liver metabolism. If liver function is abnormal, total bilirubin in blood rises. Glutamic-pyruvate transaminase (GPT) and glutamic oxaloacetic transaminase (GOT) are also commonly used markers to evaluate liver function, although these two enzymes are not only found in the liver. Nevertheless, they are more abundant in liver cells than in other organs or tissue. When the liver is damaged, inflamed liver cells release GPT and GOT into the blood in large quantities. Therefore, the amount of these factors in the blood may be useful as a basis for judging the health of liver function. In addition, the liver was made into a paraffin block and processed with H&E staining. The staining results were observed and imaged by Nikon ECLIPSE NiE orthotropic fluorescence microscope.

The first experiment was to locate the blood vessels with sectioning TPF images to confirm that ICG did not leak out of the blood vessels. After the injection of ICG into the tail, there was a relatively low scattering and absorption of laser in the 1230 nm band, so the wavelength band could penetrate the skin deeper, and the background noise was low. Because blood cells can give strong THG signals, it was possible to locate the blood vessel by using THG imaging, as shown in FIG. 15A. Before ICG injection, there was no TPF signal (see FIG. 15B). After the injection, the TPF signals appeared immediately in the region of vessel (see FIG. 15C). This result confirmed that ICG is retained in circulation and did not leak out into extravascular spaces.

By selecting the region of interest (ROI) within vessel, we quantified the TPF intensity within the vessels. The fluorescence dosimetry curve of ICG can thus be measured (as shown in FIG. 16), which is ideal to evaluate the liver function. Take the healthy control Group as an example; 90% of indigo green can be metabolized within 15 minutes (as shown in FIG. 16). The dosimetry curve can be fitted with a single exponential decay function (red curve in FIG. 16), which represents a 4.4 minutes decay time constant after injection of ICG. The decay constant can be used as an index to evaluate the liver function. For Group 1 and Group 3 four serum parameters were measured to obtain liver function information: serum albumin, total bilirubin, GPT, and GOT.

TABLE 2.1

Biochemical assay of rat serum

|  | Control Group | Group 1 | Group 3 |
| --- | --- | --- | --- |
| Albumin (g/dL) | 4.1 | 3.9 | 3.75 |
| Total bilirubin (mg/dL) | 0.4 | 0.27 | 0.6 |
| GPT (U/L) | 58.5 | 60.3 | 129 |
| GOT (U/L) | 85.5 | 89 | 265 |

From Table 2-1, our result show that GPT/GOT of Group 1 was similar to the control Group, indicating that the damage to the liver was not severe. However, the GPT and GOT of Group 3 were significantly increased, the albumin content decreased, and the total bilirubin increased. In ultrasonic images, Group 1 rats were not as homogeneous as the Control Group, but there was no significant nodules observed within them, indicating that the liver damage was not very serious. In contrast, the livers of Group 3 rats became significantly enlarged (as shown in FIG. 27C), and presented with obvious nodules (e.g., as indicated by the yellow arrow in FIG. 17D). The higher and brighter signal of local density in the ultrasound images indicated the presence of liver cirrhosis. From the corresponding fluorescence dosimetry curves shown in FIG. 18, Group 3 rats demonstrated a poor metabolic rate of ICG. At 15 minutes post injection, 45% of the initial amount was still retained in circulation. Using an exponential decay model $$\left(y = y_0 + Ae^{-\frac{x}{t}}\right)$$

to fit the curve shown in FIG. 18, Group 3 rats showed 13 minutes of decay time, which was much longer than those in the Control group and Group 1. These results demonstrated that ICG fluorescence dosimetry can be used to detect the change of liver function in the context of a liver tumor.

In order to achieve portable and compact system for medical application, the design was transferred to a single photon excitation scheme and the sensitivity of dosimetry measurement was optimized. The point measurement system described above was used to investigate the dependence of fluorescence intensity on ICG concentration. A nonlinear dependency was found (FIGS. 19A and 19B) at concentrations higher than 1 μM (or $10^{-3}$ mg/ml). In the nonlinear regime, higher concentration ICG do not increase in equal proportion, and there is a tendency of saturation. This can cause inaccuracies in dosimetry quantification. The clinical dosage for an ICG test is 0.5 mg/kg. Considering a blood volume of 70 ml per kg weight, the initial concentration is 10 μM (0.007 mg/ml), which is in the nonlinear region.

This nonlinear dependency of ICG fluorescence over concentration has been observed in the prior art (e.g., as shown in FIGS. 20A-20D). This is because ICG aggregates to form multimers, and its fluorescence intensity is weaker than that of its monomer. However, prior art studies used concentrations larger than $10^{-3}$ mg/ml and failed to note the linear regime that is suitable for correct dosimetry. The systems disclosed herein, due to the improved excitation and detection efficiencies, can measure the fluorescence signals of ICG at concentration below $10^{-4}$ mg/ml and as low as 1/10,000 of clinical concentrations, corresponding to a concentration of $7\times10^{-7}$ mg/ml (FIG. 21).

When there is no light excitation, the measured voltage is close to zero for PMT bias below 0.3 V (FIG. 21, black square). Dark noise of PMT was raised for bias voltage higher than 0.3 V. The signals from 1/10,000 clinical concentrations of ICG (FIG. 21, black diamond) were higher than the control (FIG. 21, red circle) and background. This result demonstrated that our system has a sensitivity to detect $7\times10^{-7}$ mg/ml ICG in vivo. If the initial injection concentration of ICG was 1/100 of the clinical concentration (FIG. 21, purple triangle), then the suitable operation bias voltage that can sensitively detect ICG dilution dynamics was between 0.4-0.6 V.

After the aqueous solution was tested, animal experiments were conducted. Three different doses of ICG (i.e., 1, 1/10 and 1/100 times the clinical concentration) were administered and other parameters were fixed, including excitation light output power of 50 mW and 0.4 V PMT bias voltage. A accurate dosimetry curve was achieved at 1/10 dosage (FIG. 22A) but was less accurate at the 1/100 clinical concentration. After raising bias voltage to 0.58V, an accurate dosimetry curve was measured at the 1/100 clinical concentration (FIG. 22B).

The foregoing Example confirmed that ICG fluorescence dosimetry can reflect liver function in the context of liver cancer. The excitation/collection efficiency of the measurement system was also optimized, allowing quantification of ICG concentration in the linear regime. Further, the results here show that the required dosage for in vivo dosimetry can be reduced to at least 1/100 times that of the clinical concentrations, which can greatly reduce the required dose of ICG for the evaluation of liver function.

CONCLUSION

The present disclosure may be embodied in other specific forms without departing from its spirit or essential characteristics. The described embodiments are to be considered in all respects only as illustrative and not restrictive. The scope of the invention is, therefore, indicated by the appended claims rather than by the foregoing description. While certain embodiments and details have been included herein and in the attached disclosure for purposes of illustrating embodiments of the present disclosure, it will be apparent to those skilled in the art that various changes in the methods, products, devices, and apparatuses disclosed herein may be made without departing from the scope of the disclosure or of the invention. Thus, while various aspects and embodiments have been disclosed herein, other aspects and embodiments are contemplated. All changes that come within the meaning and range of equivalency of the claims are to be embraced within their scope.

What is claimed is:

1. A method of detecting tissue ischemia, comprising:
repeatedly or constantly measuring an emission intensity of the endogenous serum chromophore transdermally from blood contemporaneously with a real time detection that the intensity or temporal change of intensity of the endogenous serum chromophore has exceeded a threshold intensity level or temporal gradient;
directing an excitation light from a continuous wave laser at the serum,
wherein the excitation light is configured to produce an excitation wavelength between 340-480 nm;
receiving an endogenous serum chromophore emission light from the excited serum by an objective lens and/or photodetector positioned to receive the luminescence signals from the endogenous chromophore,
wherein the endogenous serum chromophore emission light received from the excited serum is captured at a single photon spectrometer,
wherein the endogenous serum chromophore emission light received from the excited serum has an emission wavelength between 400-650 nm; and
determining a presence of an ischemic condition based on an intensity or a temporal change of the endogenous serum chromophore emission light by calibrating and normalizing the intensity of the endogenous serum chromophore emission light to scattering light around 467 nm and measuring a peak fluorescence intensity between 400-650 nm;
wherein determining the presence of the ischemic condition comprises calculating an optical index, the optical index comprising an arithmetic calculation of spectral and temporal variation of intensities at a plurality of wavelengths that are each associated with a principal chromophore component, determined from an excitation wavelength swept fluorescence spectra of the blood sample;
wherein based on a first determination that the ischemic condition is present, the method further comprises conducting an in vitro assay of serum marker proteins to confirm a type and/or anatomical location of the tissue ischemia, and wherein based on a second determination that the ischemic condition is not present, the method comprises monitoring the endogenous serum chromophore emission light of serum isolated at later timepoints.

2. The method of claim 1, wherein determining the presence of the ischemic condition comprises comparing the intensity or its temporal change of the endogenous serum chromophore emission light to a baseline level,
wherein the baseline level or its temporal gradient of endogenous serum chromophore have a lower value than those in the tissue ischemic condition.

3. The method of claim 1, wherein determining the presence of an ischemic condition comprises determining that the intensity or its temporal change of the endogenous serum chromophore has exceeded a threshold intensity level or temporal gradient.

4. The method of claim 1, wherein determining the presence of an ischemic condition comprises comparing a real-time measurement of the intensity or its temporal change of the endogenous serum chromophore emission light to a first timepoint or a predetermined value associated with a non-ischemic condition.

* * * * *